(12) United States Patent
Patel et al.

(10) Patent No.: US 10,028,675 B2
(45) Date of Patent: Jul. 24, 2018

(54) SOUND-BASED SPIROMETRIC DEVICES, SYSTEMS AND METHODS

(71) Applicant: University of Washington through its Center for Commercialization, Seattle, WA (US)

(72) Inventors: Shwetak N Patel, Seattle, WA (US); Mayank Goel, Seattle, WA (US); Eric C. Larson, Seattle, WA (US)

(73) Assignee: University Of Washington Through Its Center For Commercialization, Seattle, WA (US)

( * ) Notice: Subject to any disclaimer, the term of this patent is extended or adjusted under 35 U.S.C. 154(b) by 396 days.

(21) Appl. No.: 14/400,064

(22) PCT Filed: May 10, 2013

(86) PCT No.: PCT/US2013/040518
§ 371 (c)(1),
(2) Date: Nov. 10, 2014

(87) PCT Pub. No.: WO2013/170131
PCT Pub. Date: Nov. 14, 2013

(65) Prior Publication Data
US 2015/0126888 A1    May 7, 2015

Related U.S. Application Data

(60) Provisional application No. 61/645,176, filed on May 10, 2012.

(51) Int. Cl.
*A61B 5/08* (2006.01)
*A61B 5/087* (2006.01)
(Continued)

(52) U.S. Cl.
CPC .......... *A61B 5/0803* (2013.01); *A61B 5/0022* (2013.01); *A61B 5/087* (2013.01);
(Continued)

(58) Field of Classification Search
CPC ... A61B 5/0803; A61B 5/0022; A61B 5/0871; A61B 5/091; A61B 5/6898; A61B 5/087;
(Continued)

(56) References Cited

U.S. PATENT DOCUMENTS 6,241,683 B1 *  6/2001  MacKlem ............... A61B 5/091
                                                    600/529
6,436,057 B1 *  8/2002  Goldsmith ........... A61B 5/0806
                                                    600/529
(Continued)

FOREIGN PATENT DOCUMENTS

CA     2584258 A1    9/2008
JP     2004033254 A  2/2004
(Continued)

OTHER PUBLICATIONS

Chandrasekaran, et al. The natural statistics of audiovisual speech. PLoS Computational Biology. 5.7 (2009).*
(Continued)

*Primary Examiner* — Navin Natnithithadha
*Assistant Examiner* — Andrey Shostak
(74) *Attorney, Agent, or Firm* — Dorsey & Whitney LLP

(57) ABSTRACT

Devices, system, and methods generate expiratory flow-based pulmonary function data by processing a digital audio file of sound of a subject's forced expiratory maneuver. A mobile device configured to generate expiratory flow-based pulmonary function data includes a microphone, a processor, and a data storage device. The microphone is operable to convert sound of the subject's forced expiratory maneuver into a digital data file. The processor is operatively coupled
(Continued)

with the microphone. The data storage device is operatively coupled with the processor and stores instructions that, when executed by the processor, cause the processor to process the digital data file to generate expiratory flow-based pulmonary function data for assessing pulmonary function of the subject. The sound of the subject's forced expiratory maneuver can be converted into the digital data file without contact between the subject's mouth and the mobile device.

20 Claims, 16 Drawing Sheets

(51) Int. Cl.
*A61B 5/00* (2006.01)
*A61B 5/091* (2006.01)
*G06F 19/00* (2018.01)
*A61B 5/097* (2006.01)

(52) U.S. Cl.
CPC .......... *A61B 5/0871* (2013.01); *A61B 5/091* (2013.01); *A61B 5/6898* (2013.01); *G06F 19/3431* (2013.01); *A61B 5/097* (2013.01); *A61B 5/7203* (2013.01); *A61B 5/7253* (2013.01); *A61B 2562/0204* (2013.01)

(58) Field of Classification Search
CPC ..... A61B 5/7253; A61B 5/7203; A61B 5/097; A61B 2562/0204; G06F 19/3431
See application file for complete search history.

(56) References Cited

U.S. PATENT DOCUMENTS

| | | | |
|---|---|---|---|
| 7,850,619 B2 | 12/2010 | Gavish et al. | |
| 9,138,167 B1* | 9/2015 | Leydon | A61B 5/087 |
| 2001/0055297 A1 | 12/2001 | Benveniste | |
| 2002/0032387 A1* | 3/2002 | Geva | A61B 5/087 600/538 |
| 2002/0128804 A1 | 9/2002 | Geva | |
| 2003/0115051 A1 | 6/2003 | Chen et al. | |
| 2005/0032066 A1* | 2/2005 | Heng | G06F 19/3437 435/6.11 |
| 2006/0178213 A1 | 8/2006 | Ohta et al. | |
| 2007/0255122 A1* | 11/2007 | Vol | A61B 5/0295 600/301 |
| 2008/0031469 A1 | 2/2008 | Haulick et al. | |
| 2008/0243017 A1* | 10/2008 | Moussavi | A61B 5/087 600/532 |
| 2008/0281220 A1 | 11/2008 | Sharifpour | |
| 2009/0240161 A1* | 9/2009 | Sutton | A61B 5/087 600/538 |
| 2010/0305466 A1 | 12/2010 | Corn | |
| 2011/0125044 A1* | 5/2011 | Rhee | A61B 5/113 600/534 |
| 2012/0029376 A1 | 2/2012 | Meng et al. | |
| 2013/0018274 A1 | 1/2013 | O'Neill | |
| 2013/0190641 A1 | 7/2013 | Gonnen et al. | |
| 2013/0317379 A1 | 11/2013 | Brimer et al. | |
| 2014/0155708 A1 | 6/2014 | Petersen et al. | |
| 2014/0213925 A1 | 7/2014 | Chan et al. | |
| 2015/0005176 A1 | 1/2015 | Kim et al. | |

FOREIGN PATENT DOCUMENTS

| | | | |
|---|---|---|---|
| JP | 2005066044 A * | 3/2005 | |
| JP | 2012110499 A | 6/2012 | |
| WO | WO 90/04945 A1 | 5/1990 | |
| WO | WO 9004945 A1 * | 5/1990 | A61B 5/087 |
| WO | WO 2010/015865 A1 | 2/2010 | |
| WO | 2010119763 A1 | 10/2010 | |
| WO | WO 2012/038903 A2 | 3/2012 | |
| WO | 2013170131 A1 | 11/2013 | |
| WO | 2014037843 A1 | 3/2014 | |
| WO | 2014172033 A1 | 10/2014 | |
| WO | 2016154139 A1 | 9/2016 | |

OTHER PUBLICATIONS

The English-language machine translation of JP 2005066044 A is attached herewith.*
Allen, et al. Time-frequency analysis of Korotkoff sounds. IEE Seminar Digests 1997, 6 (1997).
Alshaer, et al. Phase tracking of the breathing cycle in sleeping subjects by frequency analysis of acoustic data. Int. J. Healthcare Technology and Management 2010;11(3):163-75.
Amft, et al. Analysis of chewing sounds for dietary monitoring. UbiComp 2005: Proceedings of the 7th International Conference on Ubiquitous Computing , p. 56-72, Tokyo, Japan, 11-14. Sep. 2005.
Bishara, et al. Lensfree on-chip microscopy over a wide field-of-view using pixel super-resolution. Opt Express. May 24, 2010;18(11):11181-91. doi: 10.1364/OE.18.011181.
Bland, et al. Statistical methods for assessing agreement between two methods of clinical measurement. Lancet. Feb. 8, 1986;1(8476):307-10.
Brouwer, et al. Home spirometry and asthma severity in children. Eur Respir J. Dec. 2006;28(6):1131-7. Epub Jul. 26, 2006.
Brunette., et al. Open Data Kit Sensors: A Sensor Integration Framework for Android at the Application-Level. Proceedings of the 10th International Conference on Mobile Systems, Applications, and Services (MobiSys '12), pp. 351-364.
Cochrane, et al. Intrasubject variability of maximal expiratory flow volume curve. Thorax. Apr. 1977;32(2):171-6.
European search report and opinion dated May 11, 2015 for EP Application No. 13786984.8.
Finkelstein, et al. Internet-based home asthma telemonitoring: can patients handle the technology? Chest. Jan. 2000;117(1):148-55.
Grimaldi, et al. Photoplethysmography detection by smartphone's videocamera. 2011 IEEE 6th International Conference on Intelligent Data Acquisition and Advanced Computing Systems (IDAACS). Sep. 15-17, 2011. 488-491. 10.1109/IDAACS.2011.6072801.
Grzincich, et al. Evaluation of a home telemonitoring service for adult patients with cystic fibrosis: a pilot study. J Telemed Telecare. 2010;16(7):359-62. doi: 10.1258/jtt.2010.091006. Epub Jul. 19, 2010.
Gupta, et al. mobileSpiro: Accurate Mobile Spirometry for Self-Management of Asthma. Proceedings of the 1st ACM Workshop on Mobile Systems, Applications, and Services for Healthcare. Nov. 2011. Article No. 1, 6 pages.
Harper, et al. An acoustic model of respiratory tract. IEEE Transactions in Biomedical Engineering. 2001; 48(5):543-550.
Homs-Corbera, et al. Time-frequency detection and analysis of wheezes during forced exhalation. IEEE Trans Biomed Eng. Jan. 2004;51(1):182-6.
International search report and written opinion dated Jul. 29, 2013 for PCT/US2013/040518.
Kessler, et al. Patient understanding, detection, and experience of COPD exacerbations: an observational, interview-based study. Chest. Jul. 2006;130(1):133-42.
Knudson, et al. The maximal expiratory flow-volume curve. Normal standards, variability, and effects of age. Am Rev Respir Dis. May 1976;113(5):587-600.
Kroutil, et al. Respiration monitoring during sleeping. Proceedings of the 4th International Symposium on Applied Sciences in Biomedical and Communication Techniques (Isabel '11). Oct. 2011. Article No. 33, 5 pages.
Kunzli, et al. Variability of FVC and FEV1 due to technician, team, device and subject in an eight centre study: three quality control studies in SAPALDIA. Swiss Study on Air Pollution and Lung Disease in Adults. European Respiratory Journal. Mar. 1995; 8(3):371-376.
Lafferty, et al .Conditional Random Fields: Probabilistic Models for Segmenting and Labeling Sequence Data. Proceedings of the 18th International Conference on Machine Learning 2001 (ICML Jun.-Jul. 2001), pp. 282-289.

(56) References Cited

OTHER PUBLICATIONS

Larson, et al. Accurate and Privacy Preserving Cough Sensing using a Low-Cost Microphone. UbiComp '2011 Proceedings of the 13th international conference on Ubiquitous computing pp. 375-384.

Larson, et al. SpiroSmart: Using a Microphone to Measure Lung Function on a Mobile Phone. ACM UbiComp, (2012); 280-289.

Majchrzak, et al. Improving the Compliance of Transplantation Medicine Patients with an Integrated Mobile System. 2012 45th Hawaii International Conference on System Sciences. Jan. 4-7, 2012. 2696-2705. 10.1109/HICSS.2012.319.

Miller, et al. Standardisation of spirometry. Eur Respir J. Aug. 2005;26(2):319-38.

Miravitlles, et al. Pharmacoeconomic evaluation of acute exacerbations of chronic bronchitis and COPD. Chest. May 2002;121(5):1449-55.

Murphy. Digital signal processing techniques for application in the analysis of pathological voice and normophonic singing voice. 2008. http://oa.upm.es/1079/1/KATHARINE_MURPHY.pdf.

Neuman. Vital Signs: Heart Rate. IEEE Pulse. Nov.-Dec. 2010;1(3):51-5. doi:10.1109/MPUL.2010.939179.

Nishimura, et al. Eating habits monitoring using wireless wearable in-ear microphone. ISWPC 2008. 3rd International Symposium on Wireless Pervasive Computing, May 7-9, 2008. 130-132. 10.1109/ISWPC.2008.4556181.

Olmez, et al. Classification of heart sounds using an artificial neural network. Pattern Recognition Letters 24, 1-3 (2003).

Otulana, et al. The use of home spirometry in detecting acute lung rejection and infection following heart-lung transplantation. Chest. Feb. 1990;97(2):353-7.

Pamplona, et al. NETRA: Interactive Display for Estimating Refrac-tive Errors and Focal Range. ACM Trans. Graph. vol. 29, Proceedings of SIGGRAPH 2011, pp. 77:1-77:8.

Pesola, et al. Peak expiratory flow in normals: comparison of the mini Wright versus spirometric predicted peak flows. J Asthma Oct. 2009;46(8):845-8.

Poh, et al. Motion-tolerant magnetic earring sensor and wireless earpiece for wearable photoplethysmography. IEEE Trans Inf Technol Biomed. May 2010;14(3):786-94. doi: 10.1109/TITB.2010.2042607. Epub Feb. 17, 2010.

Poh, et al. Non-contact, automated cardiac pulse measurements using video imaging and blind source separation. Opt Express. May 10, 2010;18(10):10762-74. doi: 10.1364/OE.18.010762.

Polak, et al. Telemedical system "PULMOTEL—2010" for monitoring patients with chronic pulmonary diseases. Metrology and Measurement Systems. 2010; XVII(4):537-548.

Rebuck, et al. The accuracy of a handheld portable spirometer. Chest. Jan. 1996;109(1):152-7.

Rubini, et al. Daily variations of spirometric indexes and maximum expiratory pressure in young healthy adults. Biological Rhythm Research. Apr. 2010; 41(2):105-112.

Sakka, et al. Mobispiro: A Novel Spirometer. XII Mediterranean Conference on Medical and Biological Engineering and Computing 2010 IFMBE Proceedings vol. 29, 2010, pp. 498-501.

Savitzky, et al. Smoothing and Differentiation of Data by Simplified Least Squares Procedures. Analytical Chemistry. Jul. 1964; 36(8):1627-1639.

Seemungal, et al. Time course and recovery of exacerbations in patients with chronic obstructive pulmonary disease. Am J Respir Crit Care Med. May 2000;161(5):1608-13.

Sevick, et al. Patients with Complex Chronic Diseases: perspectives on supporting self-management. J Gen Intern Med. Dec. 2007;22 Suppl 3:438-44.

Swanney, et al. Using the lower limit of normal for the FEV1/FVC ratio reduces the misclassification of airway obstruction. Thorax. Dec. 2008;63(12):1046-51. doi: 10.1136/thx.2008.098483. Epub Sep. 11, 2008.

Townsend. Spirometry in the occupational health setting—2011 update. J Occup Environ Med. May 2011;53(5):569-84. doi: 10.1097/JOM.0b013e31821aa964.

Wakita. Direct estimation of the vocal tract shape by inverse filtering of acoustic speech waveforms. IEEE Transactionson Audio and Electroacoustics. Oct. 1973; 21(5):417-427.

Walters, et al. Stability of the EasyOne ultrasonic spirometer for use in general practice. Respirology. May 2006;11(3):306-10.

"Chronic obstructed pulmonary diseases (COPD)", World Health Organization, available online at: https://web.archive.org/web/20150909052815/http://www.who.int/mediacentre/factsheets/fs315/en/, (Jan. 2015; retrieved Sep. 2015).

International Search Report and Written Opinion dated Jun. 9, 2016 for PCT/US2016/023468, 11 pages.

Receipt of first rejection for JP application No. 2015-511735 dated Apr. 10, 2017.

Allen, J et al., "Characterization of the Korotkoff sounds using joint time-frequency analysis", Physiological Measurement, 25(1):107-117, (Feb. 2004).

Crapo, R. et al., "Standardization of Spirometry, 1994 Update. American Thoracic Society", American Journal of Respiratory and Critical Care Medicine, 152(3):1107-1136, (Sep. 1995).

De Greef, L. et al., "BiliCam: using mobile phones to monitor newborn jaundice", Proceedings of the 2014 ACM International Joint Conference on Pervasive and Ubiquitous Computing: Adjunct Publication (UbiComp '14 Adjunct), pp. 39-42, (Sep. 2014).

Efron, et al., "Least Angle Regression", The Annals of Statistics, 32 (2): 407-499 (2004; Retrieved Apr. 2017).

Ericsson, "Ericsson Mobility Report: On the Pulse of the Networked Society", Available online at: https://www.ericsson.com/assets/local/mobility-report/documents/2015/ericsson-mobility-report-nov-2015.pdf, 32 pages, (Nov. 2015).

Goel, M et al., "SpiroCall: Measuring Lung Function over a Phone Call", Proceedings of the 2016 CHI Conference on Human Factors in Computing Systems (CHI '16), pp. 5675-5685 (May 2016).

Gupta, et al., "Adaptive local linear regression with application to printer color management", Image Processing, IEEE Tranactions on, 936-945, (Jun. 2008)., Jun. 2008.

Morgan, et al., "Novel signal processing techniques for Doppler radar cardiopulmonary sensing", Signal Processing, 89(1):45-66, (Jan. 2009).

Nandakumar, et al., "Contactless Sleep Apnea Detection on Smartphones", Proceedings of the 13th Annual International Conference on Mobile Systems, Applications, and Services (MobiSys '15), pp. 45-57, (May 2015).

Rafiqi, et al., "PupilWare: Towards Pervasive Cognitive Load Measurement Using Commodity Devices", Proceedings of the 8th International Conference on Pervasive Technologies Related to Assistive Environments (PETRA '15), Article No. 42, 8 pages, (Jul. 2015).

Rubini, A. et al., "Daily variations in lung volume measurements in young healthy adults", Biological Rhythm Research, 42(3):261-265, (Jun. 2011).

Sato, et al., "Application of the Vortex Whistle to the Spirometer", Transactions of the Society of Instrument and Control Engineers, 35(7):840-845, (1999; retrieved Apr. 2017).

Sato, et al., "Experimental study on the use of a vortex whistle as a flowmeter", IEEE Transactions on Instrumentation and Measurement, 49(1):200-205, (Feb. 2000).

Shen, L. et al., "Point-of-care colorimetric detection with a smartphone", Lab on a Chip, 12(21): 4240-4243, (epub Sep. 2012).

Vonnegut, B. , "A Vortex Whistle", The Journal of the Acoustical Society of America, 26(1):18-20, (Jan. 1954).

Watanabe, K. et al., "Vortex Whistle as a Flow Meter", Conference Proceedings, 10th Anniversary, Advanced Technologies in Instrumentation and Measurement Conference (IMTC/94), pp. 1225-1228, (May 1994).

Xu, W et al., "mCOPD: Mobile Phone Based Lung Function Diagnosis and Exercise System for COPD", Proceedings of the 6th International Conference on Pervasive Technologies Related to Assistive Environments (PETRA '13), Article No. 45, 8 pages, (May 2013).

Yap, Yee L. et al., "Acoustic Airflow Estimation From Tracheal Sound Power", Electrical and Computer Engineering 2002. IEEE CCECE 2002. Canadian Conference, May 2002, pp. 1073-1076.

(56) References Cited

OTHER PUBLICATIONS

Zou, et al., "Regularization and variable selection via the elastic net", Journal of the Royal Statistical Society, Series B (Statistical Methodology) 67(2), 301-320, (Apr. 2005).
"Auscultation", Wikipedia, https://en.wikipedia.org/w/index.php?title=Auscultation&oldid=79157051, Sep. 21, 2017.

* cited by examiner

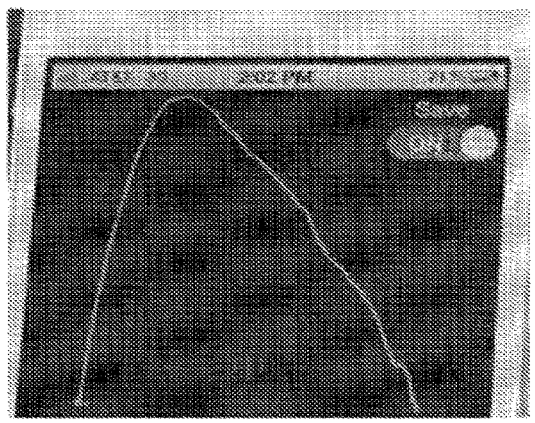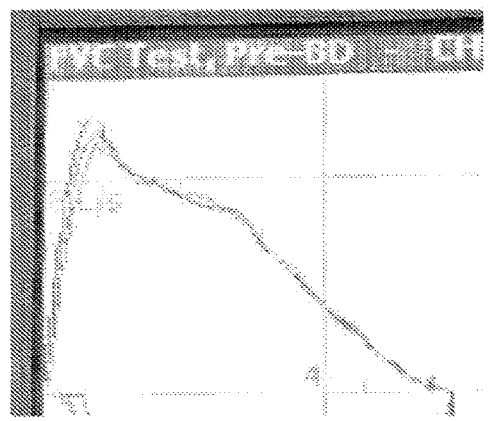
FIG. 4A
(PRIOR ART)
FIG. 4B

Sum of resonances

SOUND-BASED SPIROMETRIC DEVICES, SYSTEMS AND METHODS

CROSS-REFERENCE

This application claims the benefit of U.S. Provisional Application No. 61/645,176, filed May 10, 2012, which application is incorporated herein by reference.

BACKGROUND

Spirometry is the most widely employed objective measure of lung function and is central to the diagnosis and management of chronic lung diseases, such as asthma, chronic obstructive pulmonary disease (COPD), and cystic fibrosis. During an existing spirometry test, a patient forcefully exhales through a flow-monitoring device (e.g., through a tube or mouthpiece) that measures instantaneous flow and cumulative exhaled volume. Spirometry is typically performed in medical offices and clinics using conventional spirometers. Spirometry performed using a portable device is, however, slowly gaining acceptance. Spirometry performed with a portable device allows a patient and/or physician to more regularly monitor the patient's lung function for trends and detect changes in lung function that may need evaluation and/or treatment. Spirometry performed with a portable device may lead to earlier diagnosis of impaired lung function and may thereby result in earlier treatment of exacerbations, more rapid recovery, reduced health care costs, and/or improved outcomes.

A standard spirometer measures flow rate of air as it passes through a mouthpiece. The measured flow can be integrated to produce Flow vs. Time (FT), Volume vs. Time (VT), and/or Flow vs. Volume (FV) plots of the expiration. An example FV plot is shown in FIG. 1, which also illustrates the following spirometry parameters:

(1) Forced Vital Capacity (FVC) is the total expelled volume during the expiration, (2) Forced Expiratory Volume in one second ($FEV_1$) is the volume exhaled in the first second, (3) $FEV_1$/FVC is simply the ratio of the aforementioned parameters, and (4) Peak Expiratory Flow (PEF) is the maximum flow velocity reached during the test.

The most common clinically-reported measures are $FEV_1$, FVC, and $FEV_1$/FVC, as they are used to quantify the degree of airflow limitation in chronic lung diseases such as asthma, COPD, and cystic fibrosis. In general, a healthy result is >80% of the predicted value based on height, age, and gender (see, e.g., Knudson, R. J., Slatin, R. C., Lebowitz, M. D., and Burrows, B. The maximal expiratory flow-volume curve. Normal standards, variability, and effects of age. *The American review of respiratory disease* 113, 5 (1976)). Abnormal values are (see, e.g., Miller, M. R., Hankinson, J., Brusasco, V., et al. Standardisation of spirometry. *The European Respiratory Journal* 26, 2 (2005)):

Mild Lung Dysfunction: 60-79%
  Moderate Lung Dysfunction: 40-59%
  Severe Lung Dysfunction: below 40%

Spirometry based diagnosis is, however, more complicated than simple benchmarking. Additionally, the shape of the flow curve is subjectively evaluated by a pulmonologist, who examines the descending portion of the Flow vs. Volume curve (i.e., the portion after PEF in FIG. 1). A linear slope illustrated by first FV plot 12 is indicative of the absence of airflow limitation (i.e., normal lung function). A concave or "scooped" slope illustrated by second FV plot 14 is indicative of airflow limitation (e.g., asthma or COPD) due to differing time constants of exhaled air in different parts of the lung. Third FV plot 16 is suggestive of restrictive lung disease such as that caused by respiratory muscle weakness or pulmonary fibrosis; it can be seen as a slight bowing of the curve, a plateau, and/or a decreased FVC.

Existing Spirometry Devices

Existing spirometers are generally flow based and measure the instantaneous exhaled flow (e.g., liters/sec.). There are four prevalent types of flow-based spirometers: pneumotachographs, turbines, anemometers, and ultrasounds. Pneumotachs measure the pressure differential across a membrane as the subject exhales. These devices are affected by humidity and temperature and require daily calibration. Pneumotachs are the most prevalent spirometers in medical offices and clinics because of their accuracy.

High-end clinical spirometers can cost upwards of $5000 USD and be comparable in size to a small refrigerator. The patient sits inside an enclosure that controls humidity, temperature, and oxygen levels. Portable, ATS-endorsed spirometers (about the size of a laptop) generally cost between $1,000-$4,000 USD, and although they are relatively portable compared to their counterparts, they are still bulky, complicated devices (see, e.g., FIG. 2).

Low cost peak flow meters can cost between $10-$50 USD, but typically can only measure PEE Such low cost meters are generally about the size of a baseball and typically use a mechanical apparatus without any electronics. PET in isolation, however, is generally considered irrelevant by pulmonologists (see, e.g., Pesola, G., O'Donnell, P., and Jr, G. P. Peak expiratory flow in normals: comparison of the Mini Wright versus spirometric predicted peak flows. *Journal ref Asthma*, 4 (2009)). Digital home spirometers that report only $FEY_1$ are also commercially available ($50-$200 USD); the functionality of these meters varies widely with regard to reporting and archiving of results. For example, some digital home spirometers require patients to manually record results in journals or have a USB desktop connection. Some recent digital home spirometers can connect to a mobile phone or laptop via BLUETOOTH, but are typically more expensive (e.g., $900-$3500 USD). Recently, some low-cost (approximately $100-$200 USD) BLUETOOTH spirometers have gained excitement in the mobile health community (see, e.g., Sakka, E. J., Aggelidis, P., and Psimamou, M. Mobispiro: A Novel Spirometer. In AIEDICON '10. 2010), but their contributions are mostly in the coupling of existing hardware and Android platforms and are not ATS endorsed.

Additionally, a number of applications that claim to measure aspects of lung function have recently appeared on smartphone platforms. These smartphone applications, however, are advertised as games and have disclaimers warning not to use them for medical assessment.

Mobile Phone Based Health Sensing

There are a number of healthcare sensing systems in which external sensors are connected to smartphones. For example, Poh et al. have developed a system containing electro-optic sensors worn on the earlobe to provide photoplethysmography (PPG) data on a smartphone (see, Poh, M.-Z., Swenson, N. C., and Picard, R. W. Motion-Tolerant Magnetic Earring Sensor and Wireless Earpiece for Wearable Photoplethysmography. *Information Technology in Biomedicine, IEEE Transactions on* 14, 3 (2010)). A number of researchers have also evaluated how multiple sensors could be connected to a smartphone via an external board to collect physiological information (see, e.g., Brunette, W., Sodt, R., Chaudhri, R., et al. The Open Data Kit Sensors Framework:

Application-Level Sensor Drivers for Android. *MobiSys*, (2012); also see, e.g., Majchrzak, T. and Chakravorty, A. Improving the Compliance of Transplantation Medicine Patients with an Integrated Mobile System. *International Conference on System Sciences*, (2012)). Bishara et al. have successfully modified an existing on-device camera to perform lens-free holographic microscopy (see, Bishara, W., Su, T.-W., Coskun, A. F., and Ozcan, A. Lensfree on-chip microscopy over a wide field-of-view using pixel super-resolution. *Opt. Express* 18, 11 (2010)). Pamplona et al. have developed NETRA, a system that combines simple optical components, like lenses, with high-resolution LCD screens of smartphones to detect human eye impairments (see, Pamplona, V. F., Mohan, A., Oliveira, M. M., and Raskar, R. NETRA: interactive display for estimating refractive errors and focal range. *SIGGRAP'10*, ACM (2010)).

Researchers have also been exploring solutions that require no hardware modification. For example, Grimaldi et al. have employed a smartphone's camera and LED flashlight to measure pulse from the fingertip using photoplethysmography (see, Grimaldi, D., Kurylyak, Y., Lamonaca, F., and Nastro, A. Photoplethysmography detection by smartphone's videocamera. *IDAACS*, (2011)); while this requires a user to be in contact with the device, Poh et al. use a tablet's camera and blind source separation of color channels to measure pulse at a distance (see, Poh, M.-Z., McDuff, D. J., and Picard, R. W. Non-contact, automated cardiac pulse measurements using video imaging and blind source separation. *Opt. Express* 18, 10 (2010)).

Audio Based Health Sensing

There are also several technologies that sense medically relevant quantities using a microphone. For example, using an in-ear microphone, researchers have shown that one can detect when (and sometimes what) a person is eating (see, e.g., Amft, O. and Lukowicz, P. Analysis of chewing sounds for dietary monitoring. *UbiComp '05*, (2005); see also, e.g., Nishimura, J. and Kuroda, T. Eating habits monitoring using wireless wearable in-ear microphone. *ISWPC* 2008, (2008)). Wheeze detection with in-air and throat microphones has shown promising results in diagnosing the severity of asthma (see, e.g., Homs-Corbera, A. and Fiz, J. Time-frequency detection and analysis of wheezes during forced exhalation. *IEEE Transactions* 51, 1 (2004)). Respiratory rate is another vital sign typically sensed with body worn (see, e.g., Alshaer, H., Fernie, G. R., and Bradley, T. D. Phase tracking of the breathing cycle in sleeping subjects by frequency analysis of acoustic data. *International Journal of Healthcare Technology and Management* 11, 3 (2010)) or bedside microphones (see, e.g., Kroutil, J. and Laposa, A. Respiration monitoring during sleeping. *ISABEL '11*, (2011)). A few systems have leveraged simple, low-cost microphones to analyze signals, such as heart rate and cough. Many systems exist that extract heart rate using a mobile phone (see, e.g., Neuman, M. R. Vital Signs: Heart Rate. *Pulse, IEEE* 1, 3 (2010); see also, e.g., Olmez, T. and Dokur, Z. Classification of heart sounds using an artificial neural network. *Pattern Recognition Letters* 24, 1-3 (2003)) and, with higher-end microphones, some systems can actually be used to detect certain audible manifestations of high blood pressure referred to as Korotkoff sounds (see, e.g., Allen, J. and Murray, A. Time-frequency analysis of Korotkoff sounds. *IEE Seminar Digests* 1997, 6 (1997)). The Ubicomp community has also embraced some of this work. At Ubicomp 2011, a solution that uses the microphone on the mobile phone to detect and count coughs was presented (see, e.g., Larson, E. C., Lee, T., Liu, S., Rosenfeld, M., and Patel, S. N. Accurate and Privacy Preserving Cough Sensing using a Low-Cost Microphone. *UbiComp '11*, (2011)).

While home spirometry is slowly gaining acceptance in the medical community because of its ability to detect pulmonary exacerbations and improve outcomes of chronic lung ailments, limitations of existing home spirometer devices are inhibiting its widespread adoption. For example, challenges currently faced by home spirometry include excessive cost, patient compliance, usability, and the ability to upload results to physicians (see, e.g., Finkelstein J, Cabrera M R, H. G. Internet-based home asthma telemonitoring: can patients handle the technology. *Chest* 117, 1 (2000); see also, e.g., Grzincich, G., Gagliardini, R., and Bossi, A. Evaluation of a home telemonitoring service for adult patients with cystic fibrosis: a pilot study. *J. of Telemedicine*, (2010)). Notably, while office-based spirometry is typically coached by a trained technician, current home spirometers have no coaching, feedback, or quality control mechanisms to ensure acceptable measurements. Accordingly, improved methods and devices for accomplishing home spirometry would be beneficial.

SUMMARY

Sound-based spirometric devices, systems, and methods are provided. In many embodiments, a digital audio file of sounds of a subject's spirometric expiratory maneuver is processed to generate expiratory flow-based pulmonary function data used to assess pulmonary function of the subject. In many embodiments, the digital audio file is created by the subject exhaling the subject's full vital capacity toward a microphone held a distance away from the subject's mouth. The sound-based flow rate estimation disclosed herein enables remote spirometric testing using, for example, existing portable devices having a microphone (e.g., smartphones). Accordingly, such remote spirometric testing can enable earlier diagnosis of pulmonary disfunction, thereby enabling earlier associated treatment.

Thus, in one aspect, a mobile device is provided that is configured to generate expiratory flow-based pulmonary function data that can be used to assess pulmonary function of a patient. The device includes a microphone, a processor, and a data storage device. The microphone is operable to convert sound of a subject's forced expiratory maneuver into a digital data file. The processor is operatively coupled with the microphone. The data storage device is operatively coupled with the processor and stores instructions that, when executed by the processor, cause the processor to process the digital data file to generate expiratory flow-based pulmonary function data for assessing pulmonary function of the subject.

Because the estimation of the expiratory flow rate is based on the sound produced by the subject's expiratory maneuver, contact between the subject's mouth and the mobile device is not required. Accordingly, in many embodiments, the sound of the subject's forced expiratory maneuver is converted into the digital data file without contact between the subject's mouth and the mobile device. The subject can, however, exhale through a mouthpiece during the expiratory maneuver and the sound of the subject's expiratory maneuver can be converted into the digital data file without contact between the mouthpiece and the mobile device.

In many embodiments, expiratory flow velocity at the subject's mouth is estimated by processing the digital data file. The estimated expiratory flow velocity can then be used in conjunction with an estimate of the cross-sectional flow area of the subject's mouth to calculate expelled flow volume.

Any suitable expiratory flow-based pulmonary function data can be generated, such as any such data currently relied upon by a treating professional to assess pulmonary function of a subject. For example, the expiratory flow-based pulmonary function data can include at least one expiratory flow-based pulmonary function assessment parameter selected from the group consisting of: (1) Forced Vital Capacity (FVC), (2) Forced Expiratory Volume in one second ($FEV_1$), (3) $FEV_1/FVC$, (4) Peak Expiratory Flow (PEF), and (5) Forced Expiratory Flow between 25% and 75% of FVC (FEF(25-75)). The expiratory flow-based pulmonary function data can include at least one expiratory flow-based pulmonary function assessment metric that is based on at least one of the group consisting of: (1) FVC, (2) $FEV_1$, (3) PEF, and (4) FEF (25-75). For example, an expiratory flow-based pulmonary function assessment metric can be whether the $FEV_1$ value is within a healthy range (e.g., greater than 80% of the predicted value based on height, age, and gender), a mild lung dysfunction range (e.g., between 60-79% of the predicted value), a moderate lung dysfunction range (e.g., between 40-59% of the predicted value, or a severe lung dysfunction range (e.g., below 40% of the predicted value).

In many embodiments, superfluous sounds are modeled and removed during processing of the digital data file. For example, processing the digital data file can include modeling and removing superfluous sound generated by airflow of the forced expiratory maneuver. In many embodiments, the superfluous sound is generated by airflow of the forced expiratory maneuver through at least one of the group consisting of: (1) the subject's vocal tract, (2) the subject's mouth, and (3) the subject's surrounding environment.

In many embodiments, processing of the digital data file includes isolating and analyzing flow-related sounds. For example, in many embodiments, processing the digital data file includes isolating at least one sound related to airflow of the forced expiratory maneuver and assessing intensity of the isolated at least one sound. In many embodiments, the isolated at least one sound includes sound from at least one of the group consisting of: (1) wind shear, (2) vocal tract resonances, (3) wheezes, and (4) nasal resonances.

In many embodiments, processing the digital data file includes compensating for environment induced pressure variations. For example, processing the digital data file can include at least one of the group consisting of: (1) compensating for estimated pressure losses sustained over a distance between the subject and the microphone, and (2) compensating for at least one of reverberations and reflections of sound of the forced expiratory maneuver. In many embodiments, processing the digital data file includes using inverse radiation modeling to at least one of the group consisting of: (1) compensate for estimated pressure losses sustained over a distance between the subject and the microphone, and (2) compensate for at least one of reverberations and reflections of sound of the forced expiratory maneuver.

In many embodiments, the processing of the digital data file includes removing the effects of AC-coupling. For example, processing the digital data file can include removing the effects of AC-coupling by using at least one of the group consisting of: (1) signal power, (2) frequency characteristics, and (3) models of the subject's vocal tract.

In many embodiments, the processing of the digital data file includes removing non-linearity. For example, processing the digital data file can include removing non-linearity by combining at least two flow approximations based on the digital data file.

Processing the digital data file can include using a global model that is based on a plurality of digital data files of sound pressure levels recorded during different forced expiratory maneuvers. For example, processing the digital data file can include generating Peak Expiratory Flow (PEF) by using a global model of PEF rates of different expiratory maneuvers. Processing the digital data file can include generating Forced Vital Capacity (FVC) by using a global model of FVC values of different expiratory maneuvers. Processing the digital data file can include generating Forced Expiratory Volume in one second ($FEV_1$) by using a global model of $FEV_1$ values of different expiratory maneuvers.

In many embodiments, the mobile device is configured such that the mobile device can be calibrated relative to a particular subject. For example, processing the digital data file can include using a personalized model for a particular subject that is created by calibrating the expiratory flow-based pulmonary function data generated by the mobile device for the particular subject relative to expiratory flow-based pulmonary function data for the particular subject that is generated by another device (e.g., an ATS-endorsed spirometer at the office of a treating professional).

In another aspect, a method of generating expiratory flow-based pulmonary function data that can used to assess pulmonary function of a subject is provided. The method includes receiving a digital data file of sound of a subject's forced expiratory maneuver. The method further includes processing the digital data file to generate expiratory flow-based pulmonary function data for assessing pulmonary function of the subject.

In many embodiments of the method of generating expiratory flow-based pulmonary function data, additional acts and/or aspects are included that are analogous to any of the acts and/or aspects described herein with respect to the disclosed sound-based spirometric devices and systems, for example, the mobile device as described above.

In another aspect, a system is provided for remotely generating expiratory flow-based pulmonary function data that can be used to assess pulmonary function of a subject. The system includes a server communicatively coupled with a communication network. The server includes a processor and a data storage device operatively coupled with the processor. The data storage device stores instructions that, when executed by the processor, cause the processor to process a digital data file of sound generated by a subject's forced expiratory maneuver. The digital data file is received by the server via the communication network. The digital data file is processed to generate expiratory flow-based pulmonary function data for assessing pulmonary function of the subject.

In many embodiments of the system for remotely generating expiratory flow-based pulmonary function data, additional aspects are included that are analogous to any of the aspects described herein with respect to the disclosed sound-based spirometric devices and systems, for example, the mobile device as described above.

In many embodiments, the system for remotely generating expiratory flow-based pulmonary function data employs the communication network to transfer information to a user. For example, the system can be configured such that the expiratory flow-based pulmonary function data is transmitted over the communication network to a remote device for display on the remote device. The system can be configured such that the expiratory flow-based pulmonary function data is viewable via a website.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A shows an example expiratory flow rate curve generated and displayed by a smartphone-based spirometer, in accordance with many embodiments;

FIG. 4B shows an example expiratory flow rate curve generated by an existing spirometer for comparison with the example smartphone-based flow rate curve of FIG. 4A;

DETAILED DESCRIPTION

In many embodiments, a digitized audio file generated by recording sounds of a patient forcefully exhaling their full lung volume is processed to generate expiratory flow-based pulmonary function data that can be used to assess pulmonary function of a subject. As used herein, expiratory flow-based pulmonary function data can include any suitable expiratory flow-based data and/or information that can be used to assess the pulmonary function of a subject, such as spirometric plots and/or spirometric parameters (e.g., Flow vs. Time (FT), Volume vs. Time (VT), and/or Flow vs. Volume (FV) plots of the expiration; Forced Vital Capacity (FVC); Forced Expiratory Volume in one second ($FEV_1$); $FEV_1$/FVC; Peak Expiratory Flow (PEF)) and any suitable expiratory flow-based metric such as any suitable metric based on the aforementioned spirometric plots and/or spirometric parameters. Any suitable device, such as a portable device that includes a microphone, can be used to generate the digitized audio file. For example, the portable device can be a smartphone configured to measure lung function using the smartphone's built-in microphone. In many embodiments, the portable device includes a processor and memory storing instructions executable by the processor to process the digitized audio file to generate spirometric plots and/or spirometric parameters. In many embodiments, the digitized audio file is transferred over a communication network to be processed remotely from the portable device by a suitably configured system, such as by a server that includes a processor and memory storing instructions executable by the processor to process the digitized audio file to generate spirometric plots and/or spirometric parameters. The resulting spirometric plots and/or spirometric parameters generated remotely by the server can be at least one of: (1) transferred back over the communication network to the portable device for display to the user, (2) communicated to a health care professional (in any suitable manner, for example, over the communication network) for evaluation, and (3) stored in memory for, for example, future reference and/or use in processing similar digital audio files.

Figure 3:
FIG. 3 shows a smartphone-based spirometer, in accordance with many embodiments, being used by a subject.

As a non-limiting example, when implemented on a smartphone, a user can hold the smartphone at a suitable distance away from the user's mouth (e.g., as illustrated in FIG. 3), breathe in their full lung volume, and then forcefully exhale at the smartphone's microphone until the user's entire lung volume is expelled. The smartphone's microphone records the sounds produced by the exhalation. The resulting digital audio file is processed by the smartphone to calculate the exhaled flow rate. In many embodiments, the calculation of the exhaled flow rate includes estimating models of the user's vocal tract and estimating reverberation of sound around the user's head. The calculation of the exhaled flow rate can include calculating the envelope of the sound in the time domain, performing resonance tracking in the frequency domain, and measuring white noise gain through linear prediction. The smartphone can be configured to compute and provide flow rates and graphs similar to those found in home or clinical spirometers. For example, FIG. 4A illustrates a resulting display of spirometric flow rate generated by a smartphone-based spirometer using the approaches described herein and FIG. 4B illustrates an example display of spirometric flow rate generated by an existing spirometer. Any suitable computing device (e.g., any suitable portable computing device such as a smartphone), without any additional hardware, can be used to obtain a clinical measure of lung health.

The methods, devices, and systems disclosed herein for performing spirometry provide important advantages as compared to existing spirometers. For example, the low-cost and inherent portability of existing portable computing devices such as a smartphone enables much greater uptake of home spirometry. A portable computing device (e.g., smartphone) configured to function as a spirometer can have built-in coaching and feedback mechanisms to maximize measurement acceptability that are critically lacking in current home spirometers. A portable computing device configured to function as a spirometer can provide the capability of easy data uploading, thereby enabling longitudinal tracking of results and instantaneous alerts. A portable computing device configured to function as a spirometer can be coupled with evaluations such as symptom scores, cough sensing, and/or oximetry to provide a comprehensive disease self-management tool.

A comparison of the accuracy of the methods, devices, and systems disclosed herein for performing spirometry relative to a clinical spirometer endorsed by the American Thoracic Society (ATS) was conducted. Through a study that included 52 subjects, it was shown that a smartphone spirometer has a mean error of 5.1% for the most common measures of lung function and can be used directly out-of-the box, without any user-specific training or calibration. It was also shown that the performance of the smartphone spirometer can be improved through calibration for a particular user, thereby decreasing the mean error in estimation of lung function to 4.6%. A comparison of differences in diagnosis from five pulmonologists was conducted using measures and graphs generated from the smartphone spirometer and from a clinical spirometer. It was shown that the smartphone spirometer is effective for diagnosing not only abnormal lung function but also the degree of obstruction.

Data Collection

To evaluate and inform the design of the smartphone spirometer, a dataset of audio samples was created. 52 volunteers participated in a 45-minute study session. Table 1 presents demographic information for the 52 volunteers.

TABLE 1

Demographic information for study participants.

| Subject Demographics (N-52) | |
|---|---|
| Males (n, %) | 32 (61.5%) |
| Age (yrs) (mean, range) | 32 (18-63) |
| Height (cm) (mean, range) | 172 (152-196) |
| Reported Lung Ailments (n, %) | |
| Mild Asthma, 9 (17.3%) | Chronic Bronchitis, 2 (3.8%) |
| Cystic Fibrosis 1(1.9%) | Collapsed Lung, 1 (1.9%) |
| Abnormal Curves (n, %) | 12 (23.1%) |
| Wheeze Present (n, %) | 26 (50.0%) |
| Never Performed Spirometry (n, %) | 29 (55.8%) |

All participants in the study self-identified themselves as having none or only mild lung conditions. A custom data collection application for a smartphone was created and used to recorded subjects' exhalation sounds using the smartphone's built-in microphone (at 32 kHz) and provide feedback to the subject to coach the subject through the spirometry maneuver. Measurements were also obtained during the same session using an ATS certified standard clinical spirometer (an NSPIRE KOKO LEGEND). The KOKO LEGEND spirometer is a pneumotach spirometer and was calibrated with a 3 L syringe before each session.

Spirometry measurements are completely effort dependent and patients are coached through the spirometry maneuver by a trained technician. While using the clinical spirometer, participants were coached both orally and with gestures. With the smartphone spirometer, participants were coached with textual prompts on the smartphone's screen and only with gestures as oral prompts would have interfered with the audio recording.

Figure 1:
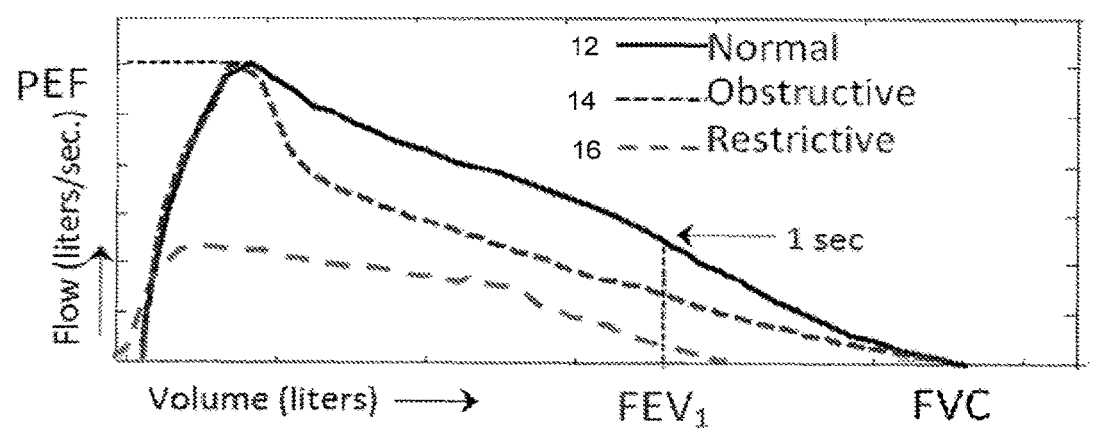
FIG. 1 shows an example Flow vs. Volume plot and related lung function parameters for spirometry expiratory maneuvers of subjects with normal, obstructive, and restrictive lung functionality.
Figure 2:
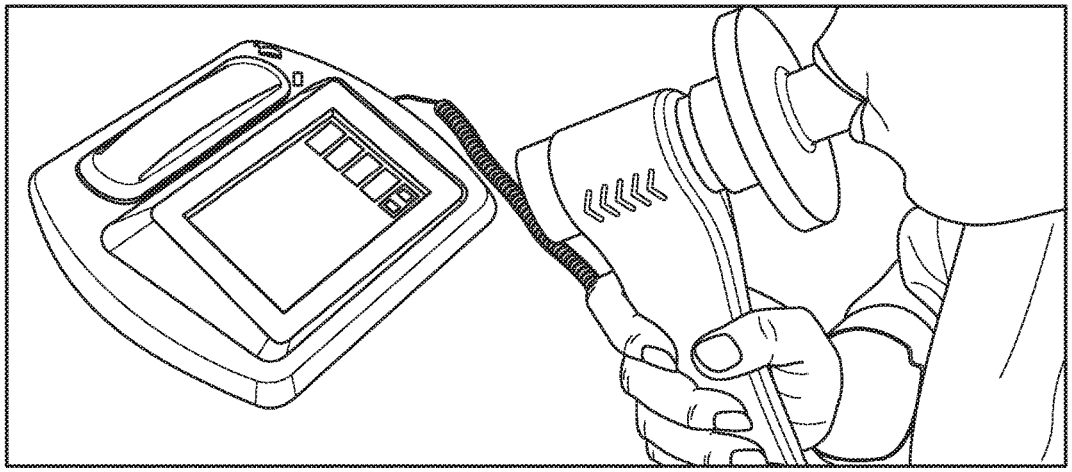
FIG. 2 shows an example portable, American Thoracic Society (ATS) endorsed spirometer.
Figure 5:
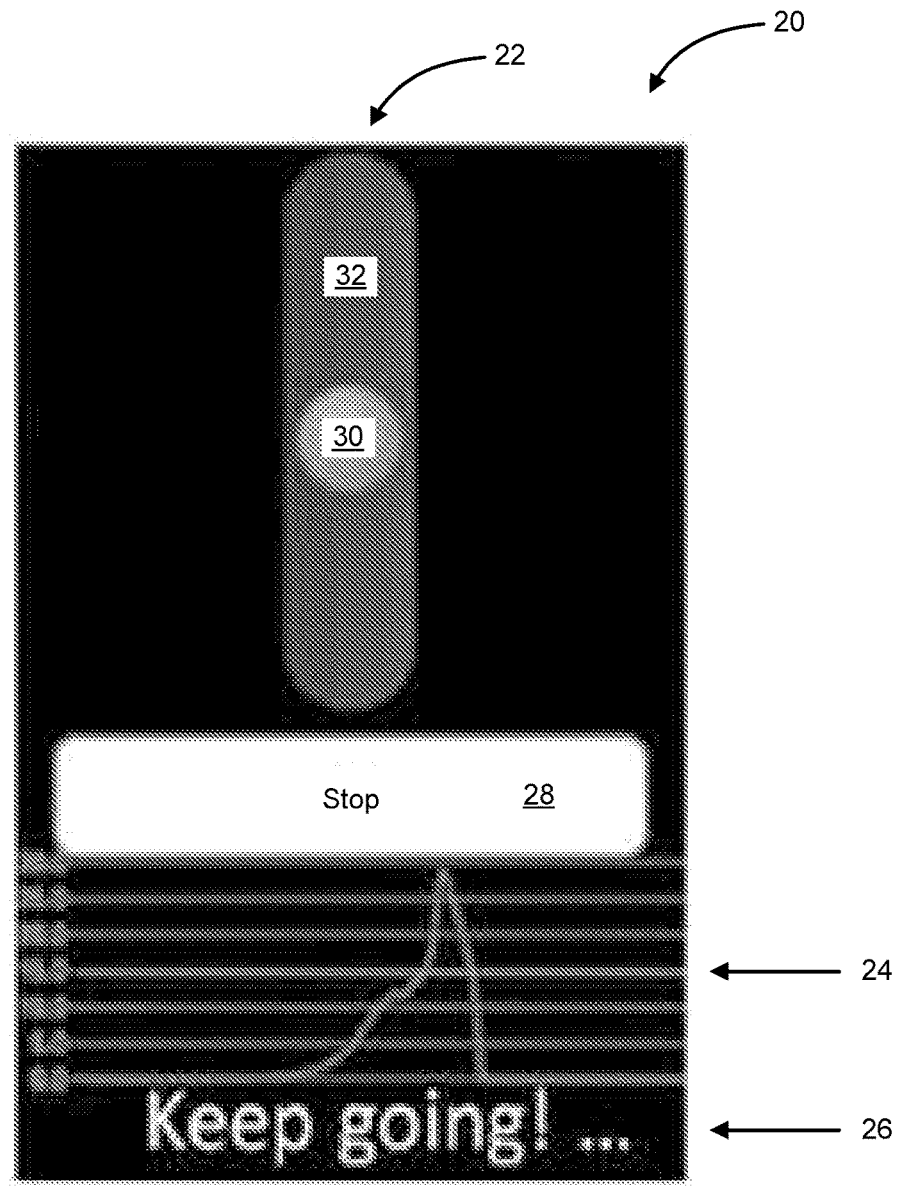
FIG. 5 shows a graphical user interface (GUI) screen displayed on a smartphone-based spirometer for coaching a subject through an expiratory maneuver, in accordance with many embodiments.

FIG. 5 shows a graphical user interface (GUI) screen 20 displayed on the smartphone for coaching the test subject through the expiratory maneuver. In many embodiments, the GUI screen 20 includes an incentive graphic 22, a real-time estimate of flow 24 (using LPC gain, discussed below), a textual prompt 26, and at least one touch screen control region 28. In the illustrated embodiment, the incentive graphic 22 includes a ball 30 displaced vertically in a cylinder 32 proportionally to the strength of the exhalations. Typically, after the initial exhalation burst, the ball 30 drops slowly to the bottom of the cylinder 32, thereby signifying the end of the test. The real-time estimate of flow 24 is displayed as a real-time visualization. The textual prompt 26 provides instructions to the test subject. The at least one touch screen control region 28 can be used to receive user input, for example, to stop the test in the illustrated screen configuration. Similar to the KOKO LEGEND spirometer, the smartphone spirometer displays an estimated Flow vs. Volume curve (e.g., as shown in FIG. 1) at the end of the effort. An estimate of exhaled volume is calculated by integrating estimated flow with respect to time.

The forced expiratory maneuver was explained to participants and they were asked to practice using the KOKO LEGEND Spirometer. Once the participants were able to perform an acceptable expiratory maneuver according to ATS criteria for reproducibility (see, e.g., Miller, M. R., Hankinson, J., Brusasco, V., et al. Standardisation of spirometry. *The European Respiratory Journal* 26, 2 (2005)), three efforts were recorded using the KOKO LEGEND Spirometer. The raw flow and volume measurements from the KOKO LEGEND Spirometer were obtained using a USB connection and custom software. The participants were then introduced to the smartphone spirometer.

Figure 6A:
FIGS. 6A through 6D show four different test configurations used to assess the impact of variations in lip posture and distance to the microphone, in accordance with many embodiments.
Figure 6B:
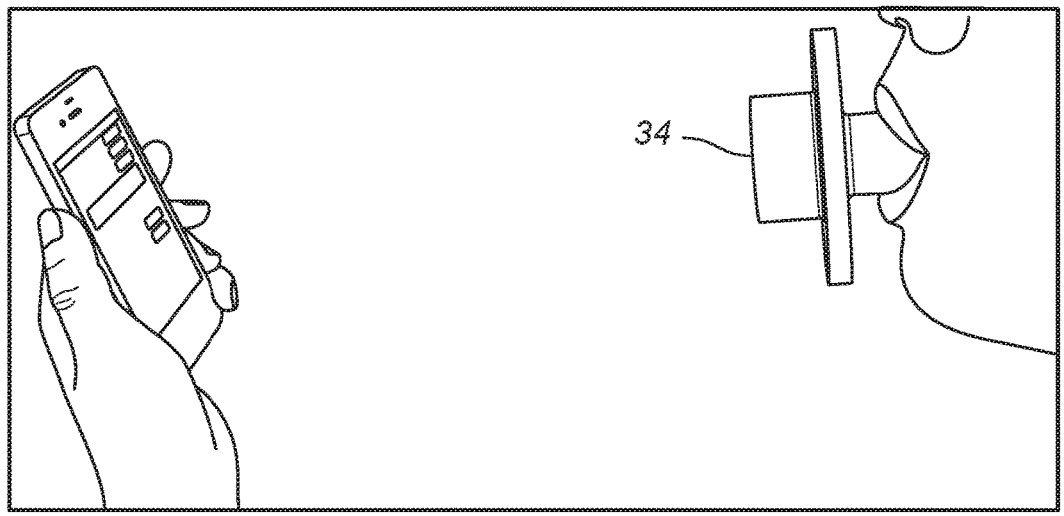
Figure 6C:
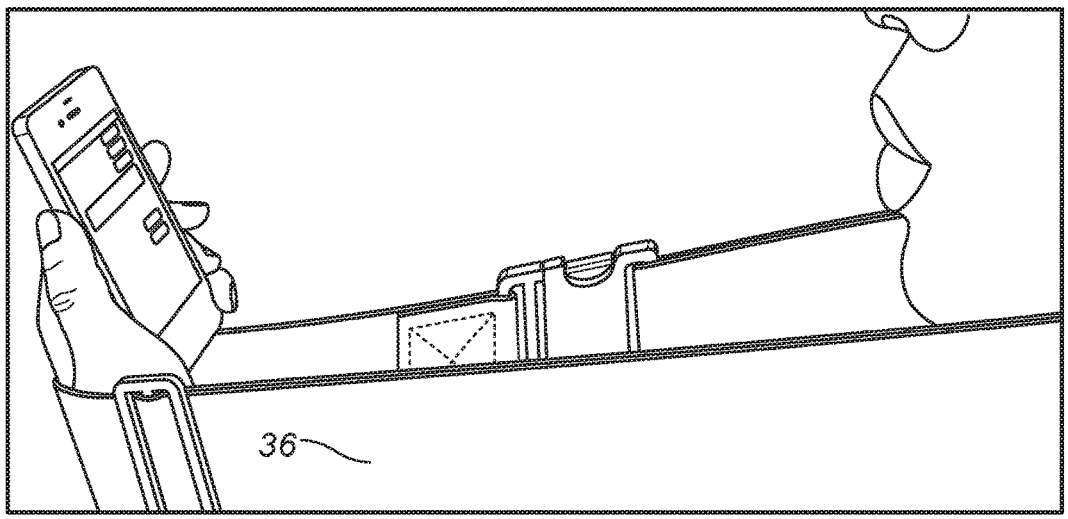
Figure 6D:
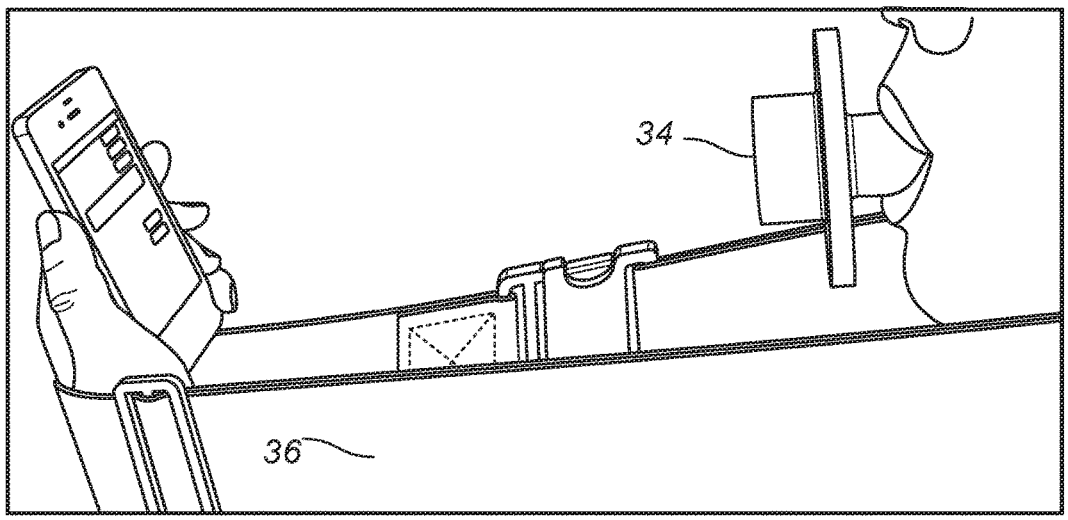

It was observed during the study that participants unintentionally varied the distance at which they held the smartphone spirometer as well as their lip posture, potentially introducing unwanted variability. To assess the impact of these unintentional variations, the participants were instructed such that they used the smartphone spirometer in four configurations, in random order: (1) with no mouthpiece 34 and no sling 36 (thereby allowing variation in distance and lip posture) as shown in FIG. 6A, (2) with a mouthpiece 34 (to maintain lip posture) as shown in FIG. 6B, (3) with a sling 36 (to maintain distance) as shown in FIG. 6C, and (4) with a mouthpiece 34 and a sling 36 (to maintain both distance and lip posture) as shown in FIG. 6D. Because a particular expiratory maneuver cannot be measured using both the KOKO LEGEND Spirometer and the smartphone spirometry embodiment, each expiratory maneuver measured using the smartphone spirometry embodiment was associated with one randomly selected acceptable curve from the KOKO LEGEND Spirometer obtained during the same session. The signals were aligned using PEF for the KOKO LEGEND Spirometer and the maximum amplitude in the audio stream from the smartphone spirometer as reference points. The audio stream was segmented automatically starting one second before and ending six seconds after the maximum audio amplitude.

Ten participants were selected to return for two more data collection sessions (two days up to two weeks apart), so as to enable assessment of the consistency of measurements from the smartphone spirometer over longer periods. The ten participants were selected based on specific demographics—an equal number of men and women, and equal number with normal and abnormal shaped spirometric curves. The abnormal shaped spirometric curves did not necessarily exhibit reduced lung function measures. In total, data was collected from 248 clinical spirometer uses and 864 uses of the smartphone spirometer.

Interestingly, six subjects were found to have abnormally shaped curves from ailments that they were unaware of Eight of the thirteen subjects who reported lung ailments produced normally shaped curves, albeit with less than expected lung function measures.

Algorithm and Theory of Operation

Sound is measured in pressure. Sound is also generated during a subject's forced expiratory maneuver by the resulting expiratory airflow. For example, sound is generated by the expiratory airflow as it passes through the subject's vocal tract, through the subject's mouth, and through the environment surrounding the subject. In the sound-based spirometric devices, systems, and methods disclosed herein, a digital audio file of sound generated during a subject's forced expiratory maneuver is processed to generate expiratory flow-based pulmonary function data that can be used to assess the pulmonary function of the patient. The digital audio file can be generated using, for example, any suitable microphone such as included in many existing portable devices.

The sound of a subject's forced expiratory maneuver at the microphone is influenced by the flow rate of air from the subject's lungs and includes superfluous sounds generated by the expiratory airflow, for example, as the expiratory airflow passes through the subject's vocal tract, through the subject's mouth, and through the subject's surrounding environment. In many embodiments, one or more superfluous sounds generated by the expiratory airflow are modeled and removed from the sound recording, thereby modifying the sound recording to remove pressure fluctuations that are less directly relatable to the rate of the expiratory airflow. These modeled and removed superfluous sounds are referred to herein as a first class of feature.

The sound of a subject's forced expiratory maneuver at the microphone also includes additional sounds that, in many embodiments, are used to infer expiratory flow rate because the intensity of these additional sounds is related to the rate of airflow. Such additional sounds include items such as wind shear, vocal tract resonances, wheezes, and nasal resonances. In many embodiments, one or more of such additional sounds are isolated and the intensity of the additional sound is used as a feature.

In many embodiments, sound pressure reductions that occur as the sound travels between the subject's mouth and the microphone and/or reverberation of sound in the subject's environment are accounted for during processing of the digital audio file. For example, in many embodiments, inverse radiation modeling (e.g., a model of a spherical baffle in an infinite plane—also known as Flanagan's sound production model) is used to account for the sound pressure reductions that occur as the sound travels between the subject's mouth and the microphone and/or reverberation of sound in the subject's environment. In many embodiments, the distance is approximated from user's height and arm length, and can be adjusted by readings from an accelerometer (e.g., if a mobile device including the microphone and the accelerometer is moved closer in).

In many embodiments, the expiratory airflow rate (distance/time—e.g., meters/second) is modeled from the combined features using non-parametric regression. Table 2 below summarizes feature categories used in many embodiments. In many embodiments, the volume of the expiratory airflow is calculated by estimating the area of the subject's mouth opening and integrating the flow. For example, the flow rate of air can be measured in m/sec. The estimated area of the subject's mouth opening can be used to convert the flow rate of air to a volumetric flow rate (e.g., liters/second). The volumetric flow rate can be directly integrated to get volume.

TABLE 2

Summary of Example Feature Categories

| Feature | Note: |
|---|---|
| Linear Predictive Gains (34 features) | Removes Vocal Tract Sounds |
| Envelope Detection (12 features) | Summative Sound Pressure, Wind Shear, AC coupling removal |
| Spectral Modeling (50 features) | Resonance Tracking, Wheeze Detection, Wind Shear, Cough |

The data collection resulted in a dataset of digitized audio samples from the smartphone spirometer. These audio samples are uncalibrated, AC-coupled measures of pressure, p(t), at the microphone of smartphone spirometer. In many embodiments, the digitized audio sample is processed to compensate for pressure losses as the sound travels from the user's mouth to the microphone, convert the pressure values to an approximation of flow, and remove the effects of AC coupling. In many embodiments, pressure losses are approximated using an inverse model of the sound reverberation around the user's head. Turbulent airflow, as it passes through a fixed opening (e.g., the user's mouth), has a characteristic pressure drop, which, in many embodiments, is used for converting pressure into flow. In many embodiments, at least one of: (1) signal power and frequency characteristics, and (2) models of the vocal tract is used to remove the effects of AC-coupling and refine the flow approximations.

In many embodiments, regression is used to combine these flow approximations and remove non-linearity. In many embodiments, the processing of the digitized audio sample(s) includes compensation and feature extraction (as illustrated in FIGS. 7A through 7I) and machine learning regression (as illustrated in FIG. 8).

Distance and Flow Compensation

In many embodiments, the first stage in processing a digitized audio sample (e.g., obtained by the smartphone spirometer) is to use inverse radiation modeling to compensate for pressure losses sustained over the distance from the user's mouth to microphone and for reverberation/reflections caused in and around the user's body. Any suitable inverse radiation modeling can be used. For example, the transfer function from the microphone to the user's mouth can be approximated by equation 1, which is corresponds to a spherical baffle in an infinite plane.

$$H(e^{j\omega}) = \frac{P(e^{j\omega})}{P_{lips}(e^{j\omega})} \sim \frac{j\omega C_{head}}{D_{arm}} \exp\left(-\frac{j\omega D_{arm}}{c}\right) \quad \text{equation (1)}$$

where: $D_{arm}$ is the arm length (e.g., approximated from user's height);
$C_{head}$ is the head circumference (e.g., approximated from user's height); and
$c$ is the speed of sound The transfer function inverse is applied by converting it to the time domain, $h_{inv}(t)$, and using Finite Impulse Response (FIR) filtering with the incoming audio. Once applied, the output is an approximation of the pressure at the lips, $p_{lips}(t)$.

The pressure at the lips ($p_{lips}(t)$) is then converted to a flow rate. For turbulent airflow, equation (2) is a non-linear equation that can be used to convert pressure drop across the lips to flow rate through the lips.

$$u_{lips}(t) \sim 2\pi r_{lips}^2 \sqrt{2p_{lips}(t)} \quad \text{equation (2)}$$

where: $r_{lips}$ is the radius of the user's mouth opening (a constant resistance across frequency).

Some scaling constants have been removed from each of equation (1) and (2) and the equations are only proportional. The scaling constants were removed because p(t) is not calibrated, so $u_{lips}(t)$ is only proportional to the actual flow rate. Moreover, it is unclear how well these equations (1) and (2) perform when using approximations of $D_{arm}$, $C_{head}$, and $r_{lips}$; and how non-linearity in the microphone affects inverse modeling. Therefore, in many embodiments, each measure p(t), $p_{lips}(t)$, and $u_{lips}(t)$ is used for feature extraction and regression is used to determine which features are most stable.

Feature Extraction

Figure 7A:
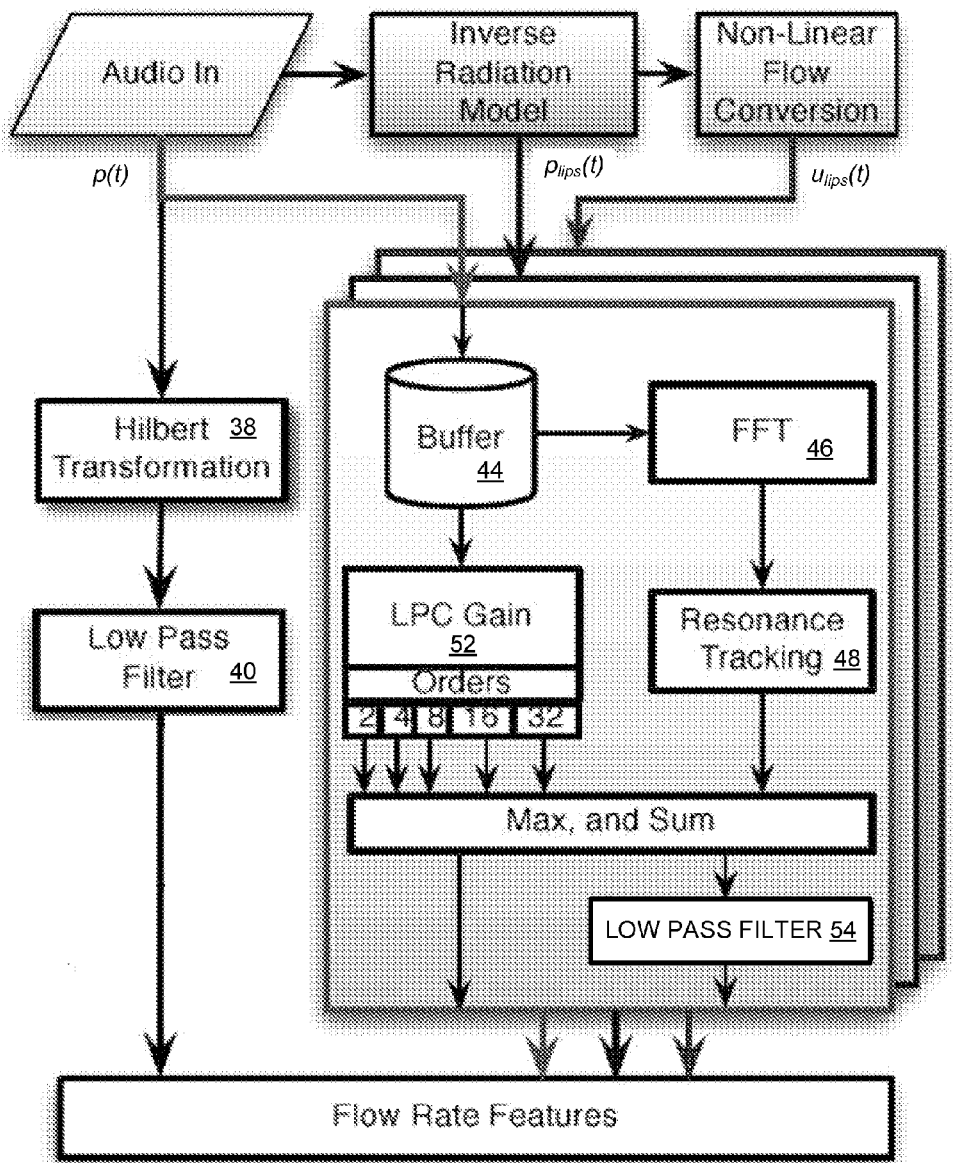
FIG. 7A schematically illustrates processing acts used to process a digital audio file of sounds of a subject's expiratory maneuver to produce a plurality of flow rate approximations, in accordance with many embodiments.
Figure 7B:
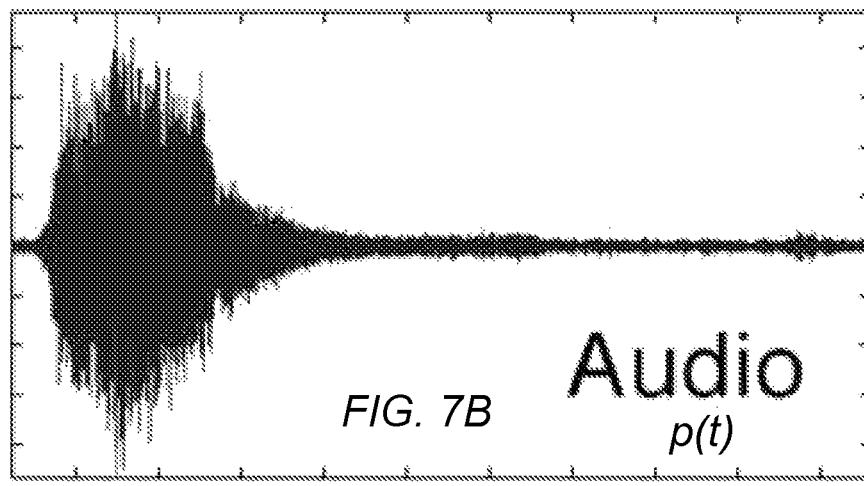
FIG. 7B illustrates example measures of pressure, p(t), in a digital audio file of sounds of a subject's expiratory maneuver, in accordance with many embodiments.
Figure 8:
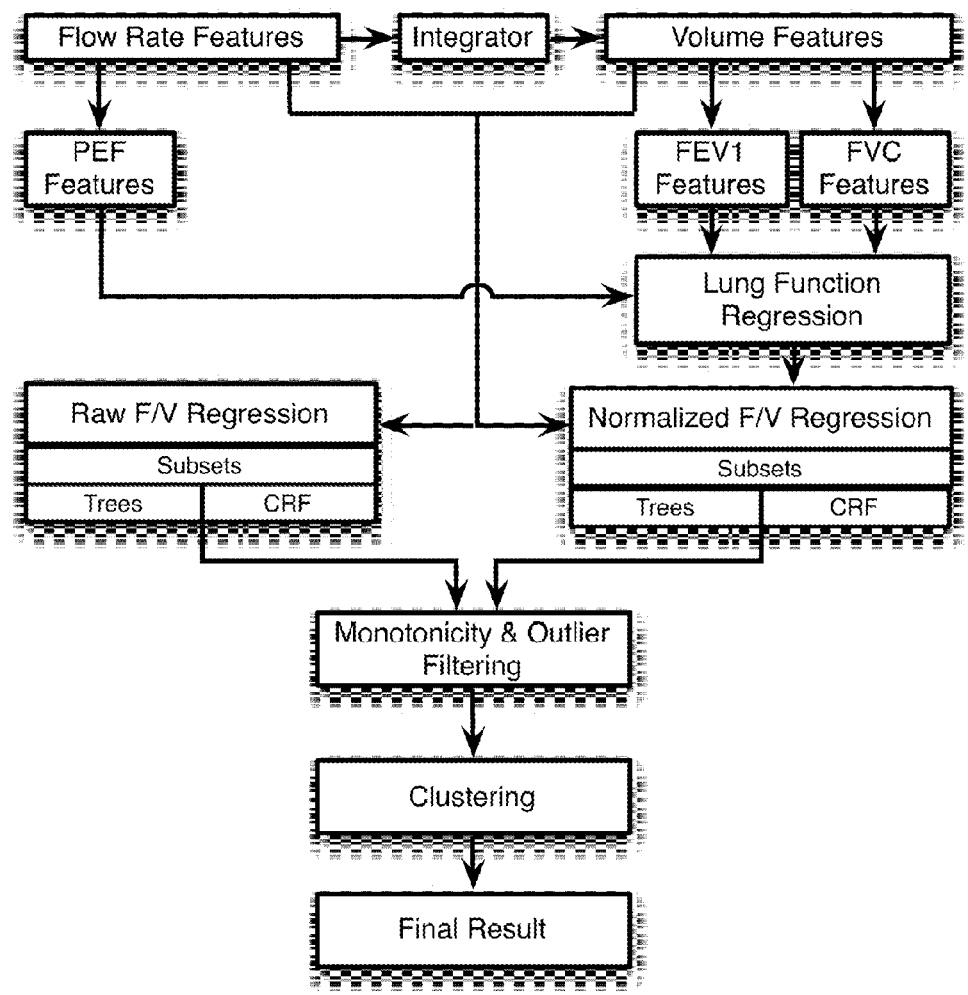
FIG. 8 schematically illustrates processing acts used to process the flow rate approximations of FIGS. 7G through 7I to generate a final Flow vs. Volume curve and corresponding final lung function parameters PEF, $FEV_1$, and FVC, in accordance with many embodiments.

Referring to FIG. 7A, each measure, p(t), $p_{lips}$, (t), and $u_{lips}(t)$, is a high frequency, AC-coupled signal, from which a separate volumetric flow rate is approximated. In many embodiments, approximating volumetric flow rate from these signals includes using three transformations of these signals: (1) envelope detection, (2) spectrogram processing, and (3) linear predictive coding (LPC). Each envelope of the signals (p(t), $p_{lips}$, (t), and $u_{lips}(t)$) can be assumed to be a reasonable approximation of the flow rate because it is a measure of the overall signal power (or amplitude) at low frequency. Spectrogram processing is used to extract resonances. In the frequency domain, resonances are assumed to be amplitudes excited by reflections in the vocal tract and mouth opening and therefore should be proportional to the flow rate that causes them. Linear prediction is then used as a flow approximation. Linear prediction assumes that a signal can be divided into a source and a shaping filter and it estimates the source power and shaping filter coefficients. The "filter" in this case is an approximation of the vocal tract (see, e.g., Wakita, H. Direct estimation of the vocal tract shape by inverse filtering of acoustic speech waveforms. *Audio and Electroacoustics, IEEE Transactions on* 21, 5 (1973), 417-427). The "source variance" is an estimate of the white noise process exciting the vocal tract filter and is an approximation of the power of the flow rate from the lungs. The implementation of each stage is explained below in turn.

Figure 7C:
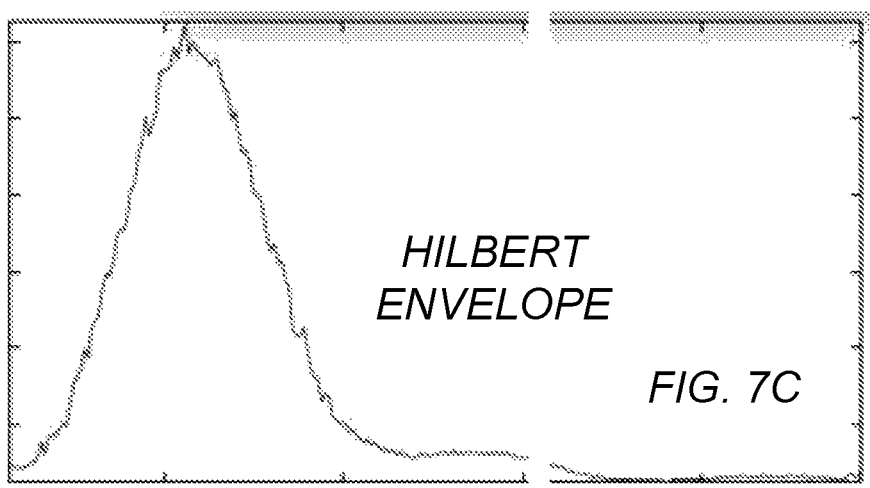
FIG. 7C illustrates an example Hilbert Envelope of one of: (1) measures of pressure, p(t), at the microphone, (2) estimated measures of pressure, p_lips(t), at the subject's mouth, and (3) estimated measures of flow, u_lips(t), at the subject's mouth, in accordance with many embodiments.

Envelope Detection:

These features measure the energy of the data in each audio file over different frames. The low frequency envelope of the signal (proportional to power here) can be extracted by squaring the signal and low pass filtering at a sub 1 Hz cutoff. The time domain envelope can also be taken using the Hilbert envelope. The Hilbert transform 38 of the signal can be taken and added back to the original signal. Low pass filtering 40 can then be used to extract the envelope using cascaded second order system filters (an example envelope is shown in FIG. 7C). Each signal (p(t), $p_{lips}$(t), and $u_{lips}(t)$) can be down-sampled 42 to have the same sampling rate as the spectrogram and linear prediction models. Different estimations of the envelopes can be ascertained from using slightly different low pass filters on the squared data and Hilbert transformed data. In one embodiment, 12 features are used.

Figure 7D:
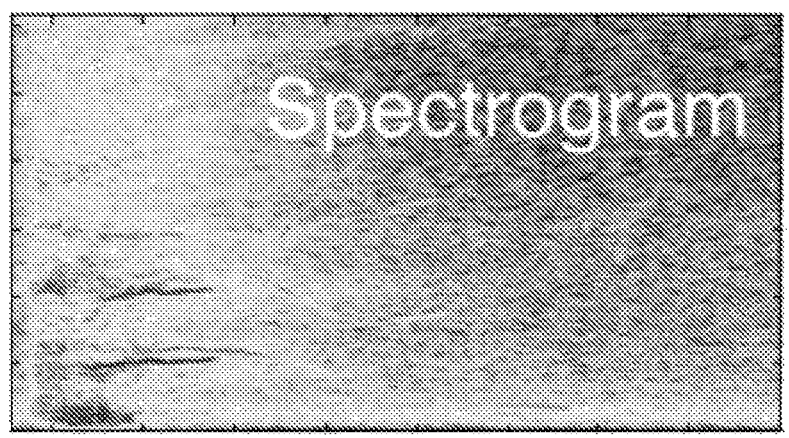
FIG. 7D illustrates an example magnitude spectrogram of one of: (1) measures of pressure, p(t), at the microphone, (2) estimated measures of pressure, p_lips(t), at the subject's mouth, and (3) estimated measures of flow, u_lips (t), at the subject's mouth, in accordance with many embodiments.
Figure 7E:
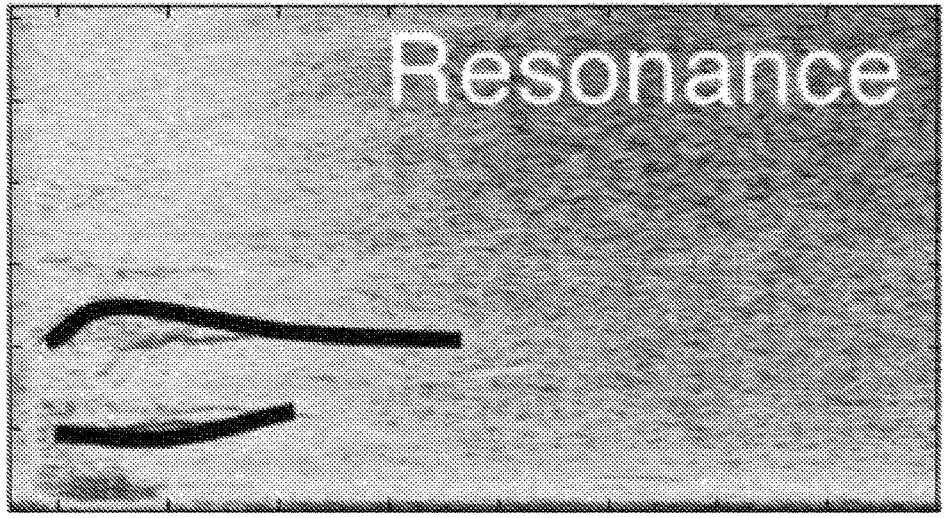
FIG. 7E shows a plot of resonances generated by processing the magnitude spectrogram of FIG. 7D, in accordance with many embodiments.
Figure 7F:
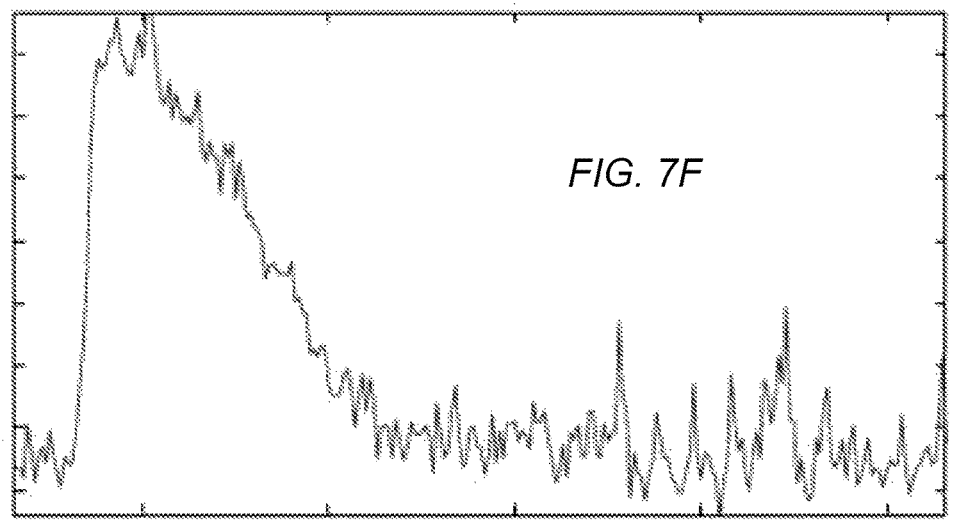
FIG. 7F shows average resonance magnitudes generate by processing the magnitude spectrogram of FIG. 7D, in accordance with many embodiments.
Figure 7G:
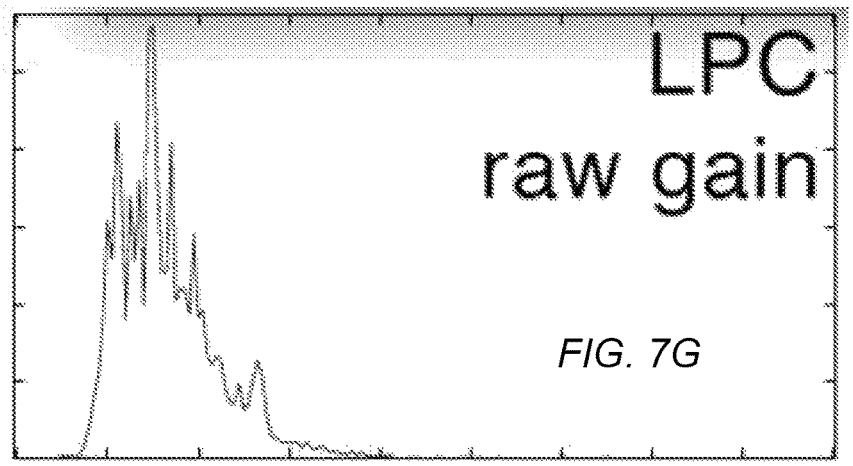
FIG. 7G shows an example resulting flow rate approximation generated by processing p(t) per the processing acts of FIG. 7A, in accordance with many embodiments.
Figure 7H:
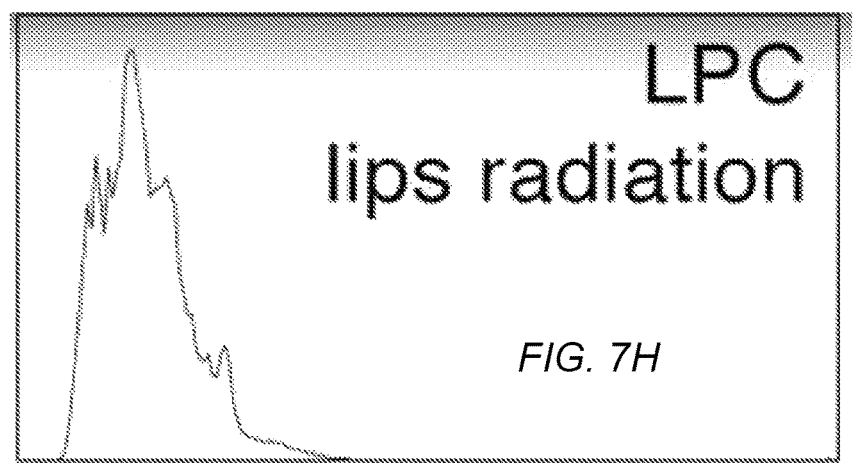
FIG. 7H shows an example resulting flow rate approximation generated by processing p_lips(t) per the processing acts of FIG. 7A, in accordance with many embodiments.
Figure 7I:
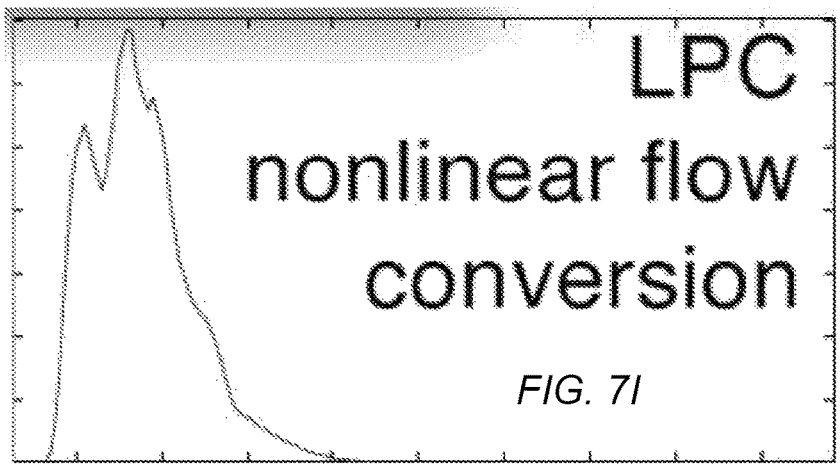
FIG. 7I shows an example resulting flow rate approximation generated by processing u_lips(t) per the processing acts of FIG. 7A, in accordance with many embodiments.

Spectrogram Processing:

In many embodiments, during the forced exhalation, the audio from the phone is buffered 44 into 30 ms frames (with 50% overlap between frames). A spirometry exhalation typically lasts from four to seven seconds, resulting in 250-500 frames per exhalation. Each frame can then be windowed using a hamming window and the Fast Fourier Transform |FFT|$_{dB}$ 46 is taken to produce the magnitude spectrogram of the signal (an example of which is illustrated in FIG. 7D). The resonances can be extracted (resonance tracking 48) using local maxima in each FFT frame, calculated over a sliding window (see, e.g., FIG. 7E). Any maxima that is greater than a suitable threshold, for example 20% of the global maximum, can be saved. After all frames have been processed, in order to preserve only large and relatively long resonances, any resonance less than 300 ms can be discarded as noise. Finally, the average resonance magnitude in each frame is calculated (Mean 50) and saved (see, e.g., FIG. 7F).

Linear Prediction Processing (52):

In many embodiments, the audio signal is again windowed into 30 ms overlapping frames. For each frame a number of LPC models can be taken, for example, with filters orders of 2, 4, 8, 16 and 32 (increasing vocal tract complexity). The approximated "source power" that excites the filter can be saved for each frame as an approximation of the flow rate. Examples of the LPC from using p(t), $p_{lips}$(t), and $u_{lips}(t)$ are shown FIG. 7G, FIG. 7H, and FIG. 7I, respectively. Various combinations of LPC order can be used to ascertain different estimates of the vocal tract. In one embodiment this results in 34 different estimates. The audio signal can be filtered by the inverse LPC model, which leaves only noise from random noises, such as wind shear. Additionally, the bandwidth and magnitude of the largest resonance from the LPC model can be calculated and used as another spectral estimate of the signal. By isolating the resonances between 400 and 900 Hz with different LPC models, the reverberation of the lips can be estimated as the lips typically resonate in this frequency range. In one embodiment, this adds to the number of spectral features, totaling 50.

Post Feature Processing:

In many embodiments, once the approximated flow rates are returned they are denoised using a Savitsky-Golay polynomial filter of order 3 and size 11 (Low Pass Filter 54) (see, e.g., Savitzky, A. and Golay, M. J. E. Smoothing and Differentiation of Data by Simplified Least Squares Procedures. *Analytical Chemistry* 36, 8 (1964)). A third order polynomial can be fit inside a moving window and is robust to many types of noise while keeping the relative shape of the most prominent signal intact. The filtered and non-filtered signals are both fed as features to the subsequent regression stage.

Machine Learning Regression

The above-described feature extraction results in a number of uncalibrated approximations of the flow rate. Referring to FIG. 8, these features are used in two different regressions—one to attain specific lung function measures and a second to attain the relative shape of the curve.

Folding:

The participants in the dataset can be folded into several training subsets, providing a number of diverse models that can be combined to create a global model. For example, one subset randomly divides the participants into ten folds equally. Another subset divides participants with wheezes together into ten folds. Another subset divides the dataset into ten folds, but ensures there are equal numbers of abnormal and normal curves to train on. Still other subsets can be created based on if subjects have a throat clear or based on their level of obstruction. Each subset is used to create a different regression model and the ensemble can be clustered together to form one decision. Note that for any subset a participant in a testing fold is never used in the training fold. Moreover, to investigate "personalizing" the models, augmented folds were created that contain data from repeat sessions (e.g., for the 10 subjects who performed three sessions spanning multiple days). In this way, "personalized" models are trained using data from the same participant (but on different days) mixed with data from the general model. General and personalized models are evaluated separately. Additionally, past features of different patients can be saved so that new curves can be compared to their empirical average for a given feature. Features can then be scaled by dividing them by empirical averages for a given participant. This adds new "personalized" features to the model without the need for curves from a spirometer for a participant (i.e., semi-supervised learning).

Lung Function Regression:

The feature extraction creates a number of features at 15 ms time steps that approximate flow rate over time. Referring to FIG. 8, by treating each feature as a flow rate, regression can be used to directly yield PEF, $FEV_1$, and FVC. For example, PEF is defined as the maximum flow reached in a single effort. Thus, for a curve in a given fold, the maximum of each feature can be used to regress to the PEF. Integrating flow with respect to time gives the volume of air exhaled. Thus for FVC, the integration of each feature is accomplished. For $FEV_1$, the integration of the features during the first second is used. These new features can be combined with other demographic features such as gender and age, weight, and height range. These features can be quantized to discrete ranges to prevent overfitting.

In many embodiments, regression is implemented using bagged decision trees and mean square error; 100 trees are used in each forest. Each training subset can be used to predict lung function for a given test instance, resulting in an ensemble of predictions. The final decision can be made by clustering the ensemble using k-means (k=2). The centroid of the cluster with the most instances can be the final prediction of PEF, $FEV_1$, and/or FVC.

Curve Shape Regression:

The shape of the curve is a more difficult and involved regression. Instead of a single measure to regress to for each curve, flow rate and volume can be measured for each frame (e.g., 15 ms frame) of the curve. Preferably, the regression should use not only the feature value, but also the correlations across time because flow rates that are close in time should also be close in value. To exploit this, a conditional random field (CRF) (see, e.g., Lafferty, J., McCallum, A., and Pereira, F. Conditional Random Fields: Probabilistic Models for Segmenting and Labeling Sequence Data. *Proc. Int. Conf on Machine Learning*, (2001)) and a bagged decision tree regression can be employed. However, because CRFs are used to classify time series into classes (and not continuous values), the flow rates are divided into 11 classes by rounding to the nearest 0.5 L (0-0.25 L becomes class "0," 0.25-0.75 L becomes class "1," etc.). For each curve in each fold, a CRF is run on the entire curve as one segment. The resulting CRF logs likelihoods of each instance are combined with the original features to form a new instance vector for each frame (i.e., stacking).

In order to reduce the complexity for CRF based regression, normalized flow-volume curves can be generated in support of obtaining the correct shape of the curve. In many embodiments, each feature is normalized. Finally, a bagged decision tree regression is used to obtain the flow rate at each time step. The shape of the curve is the main aim of this regression. Once the shape is obtained, the curve is scaled by measures from the lung function regression stage. This process can then be repeated for the volume (i.e., each feature is integrated and the volume curve is regressed to instead of the flow curve). This results in separately calculated flow and volume curves. Much like the regression for lung function measures, the curves from different subsets are clustered using k-means with k=2 (in this case the area under the curve is used to cluster). Before clustering, outliers can be removed and curves that are physically impossible can be discarded (e.g., the volume cannot be monotonically increasing). Finally, the average of the curves in the largest cluster can be taken as the final Flow vs. Volume curve.

Methods and Systems

Figure 9:
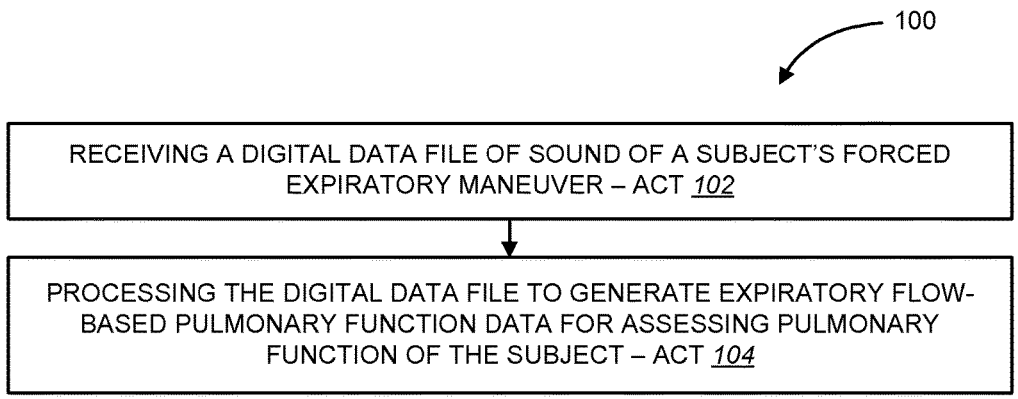
FIG. 9 is a simplified block diagram of acts of a method, in accordance with many embodiments, of generating expiratory flow-based pulmonary function data by processing a digital audio file of sound of a subject's forced expiratory maneuver.

While the foregoing description has been presented in the context of the smartphone spirometer, the approaches disclosed herein, which include processing a digital audio file of sound produced by a subject's forced expiratory maneuver to generate expiratory flow-based pulmonary function data, for example, to measure and/or estimate expiratory flow rate and/or corresponding lung function parameters, can be embodied in any suitable method (e.g., in the methods 100 and 110 described herein), device, and/or system. For example, FIG. 9 is a simplified diagram of acts of a method 100, in accordance with many embodiments, of generating expiratory flow-based pulmonary function data.

The method 100 includes receiving a digital data file of sound of a subject's forced expiratory maneuver (act 102). The method 100 further includes processing the digital data file to generate expiratory flow-based pulmonary function data for assessing pulmonary function of the subject (act 104). Any of the suitable approaches described herein can be used to process the digital data file to generate the expiratory flow-based pulmonary function data.

Figure 10:
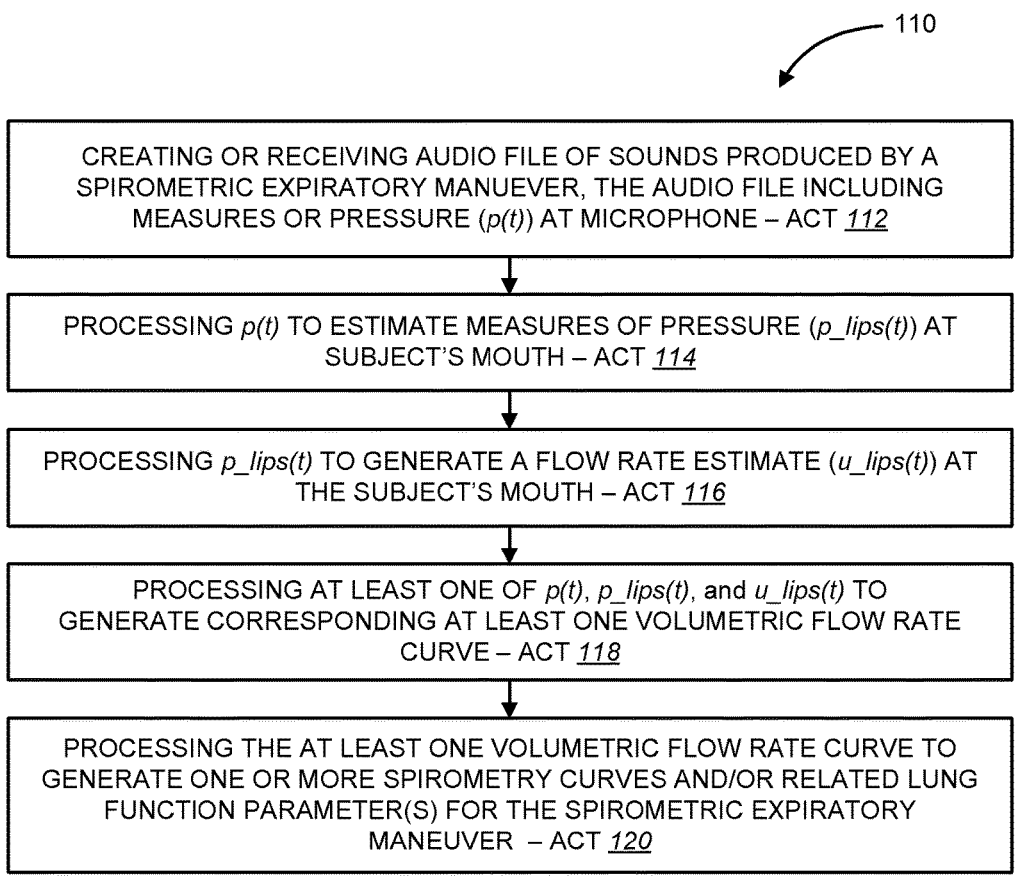
FIG. 10 is a simplified block diagram of acts of a method for processing a digital audio file of sounds of a subject's expiratory maneuver to generate a spirometry curve and/or related lung function parameters, in accordance with many embodiments.

FIG. 10 is a simplified diagram of acts of a method 110, in accordance with many embodiments, of measuring and/or estimating expiratory volumetric flow rate and/or corresponding lung function parameters.

The method 110 includes creating or receiving a digital audio file of sounds produced by a spirometric expiratory maneuver (act 112). The most common spirometric expiratory maneuver is the basic forced volume vital capacity (FVC) test. Generally, during a FVC test, the subject is directed to take the deepest breath possible, and then exhale as hard as possible, for as long as possible, preferably at least 6 seconds. In many embodiments of the method 110, the digital audio file is created as described herein via the subject exhaling toward a microphone that is used to create the digital audio file. The digital audio file contains uncalibrated, AC-coupled measures of pressure, p(t), at the microphone. The digital audio file can be created or received in any suitable fashion. For example, the digital audio file can be created at a remote location and then received via transmission over any suitable communication network, such as the internet.

The method 110 further includes processing the measures of pressure, p(t), to estimate corresponding measures of pressure (p_lips(t)) at the subject's mouth (act 114). For example, p(t) can be processed to generate p_lips(t) using any suitable approach including, for example, using any suitable inverse radiation modeling such as described herein.

The estimated measures of pressure at the subject mouth ($p_{lips}(t)$) are then processed to generate a flow rate estimate ($u_{lips}(t)$) at the subject's mouth (act 116). For example, $p_{lips}(t)$ can be processed using equation (2) as described herein.

At least one of p(t), $p_{lips}(t)$, and $u_{lips}(t)$ is then processed to generate a corresponding at least one volumetric flow rate curve (act 118). For example, in many embodiments, each of p(t), $p_{lips}(t)$, and $u_{lips}(t)$ is separately processed to generate corresponding flow rate curves. Any suitable approach can be used to process p(t), $p_{lips}(t)$, and $u_{lips}(t)$ to generate corresponding volumetric flow curves including, for example, (1) envelope detection, (2) spectrogram processing, and (3) linear predictive coding (LPC) as described herein.

The separately calculated flow rate curves are then processed to generate one or more resulting spirometry curves and/or related lung function parameters for the spirometric expiratory maneuver (act 120). For example, the separately calculated flow rate curves can be clustered using k-means with k=2 with the average of the curves in the largest cluster being used to generate the resulting spirometry curves and/or related lung function parameters for the spirometric expiratory maneuver.

Figure 11:
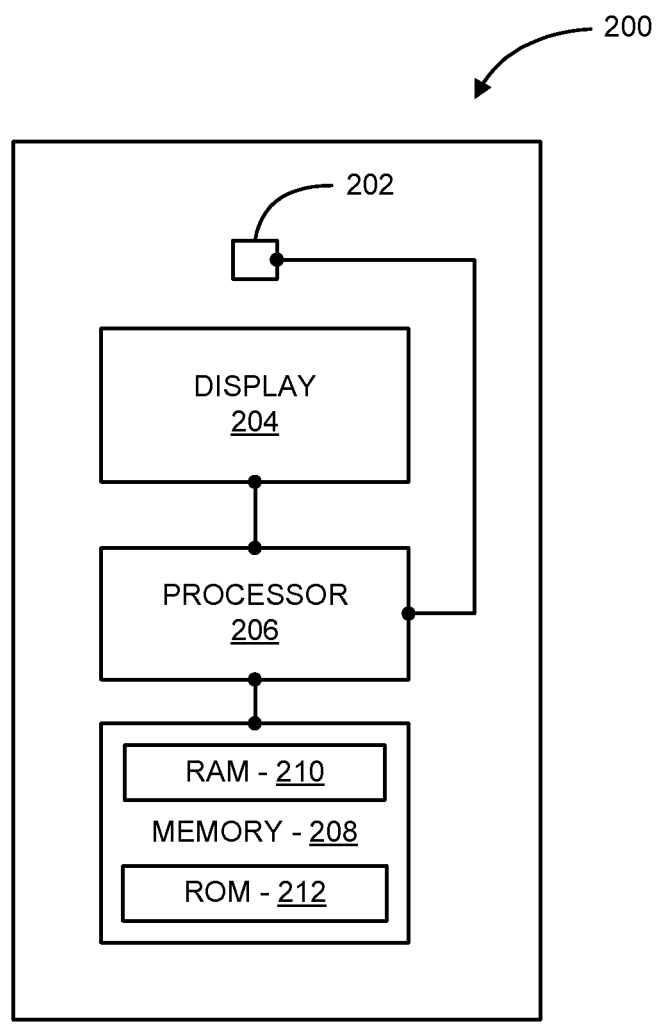
FIG. 11 schematically illustrates a mobile device based spirometer, in accordance with many embodiments.

FIG. 11 is a simplified schematic diagram of the mobile device 200, in accordance with many embodiments. The mobile device 200 includes a microphone 202, a display 204, a processor 206, and memory 208. The microphone 202, display 204, and the memory 208 are communicatively coupled with the processor 206. The memory 208 can include any suitable configuration of tangible storage medium including, for example, a random access memory (RAM) 210 and read only memory (ROM) 212 as shown. In many embodiments, the memory 208 stores instructions executable by the processor 206 for causing the processor to process a digital audio file created by the microphone 202 of sounds produced by a subject's spirometric expiratory maneuver using any of the approaches as described herein so as to generate one or more spirometry curves and/or one or more related lung function parameters for the subject's spirometric expiratory maneuver. The resulting spirometry curves and/or related lung function parameters can then be displayed on the display 204.

Figure 12:
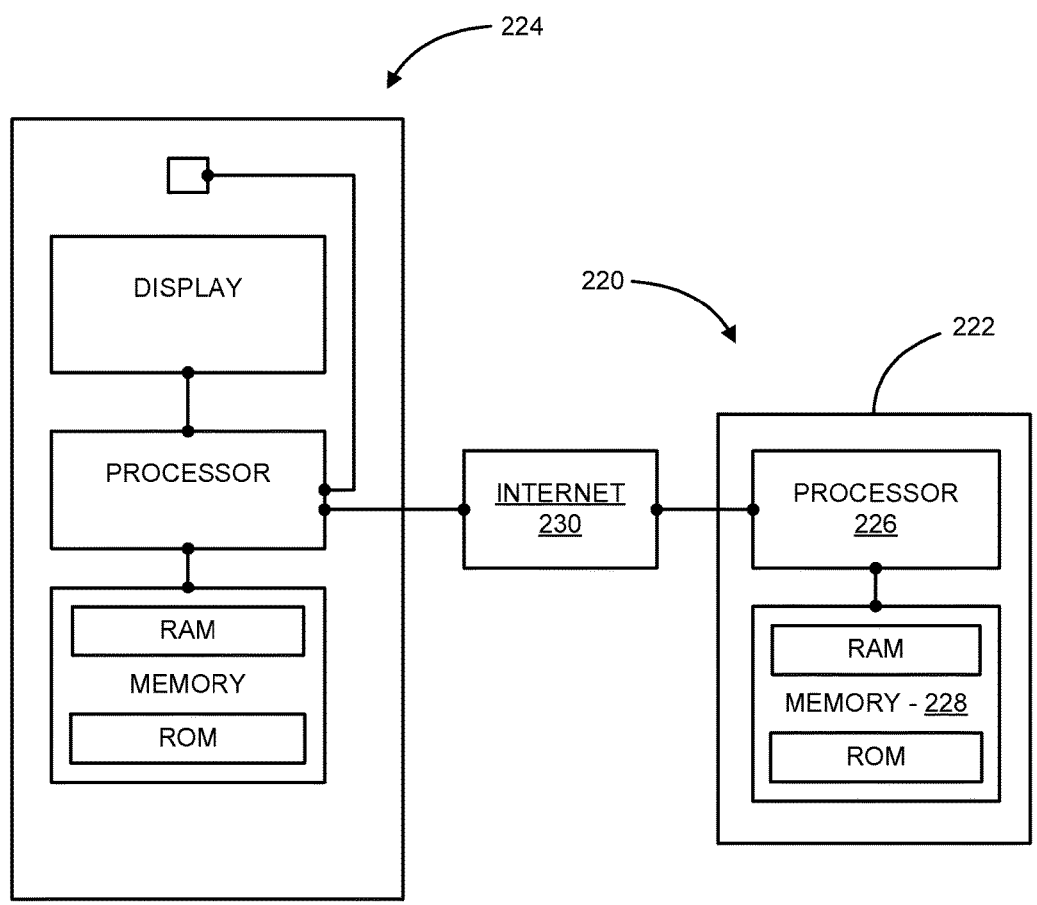
FIG. 12 schematically illustrates a system for remotely processing a digital audio file of sounds of a subject's expiratory maneuver to generate data used to assess pulmonary function of a patient, in accordance with many embodiments.
Figure 13A:
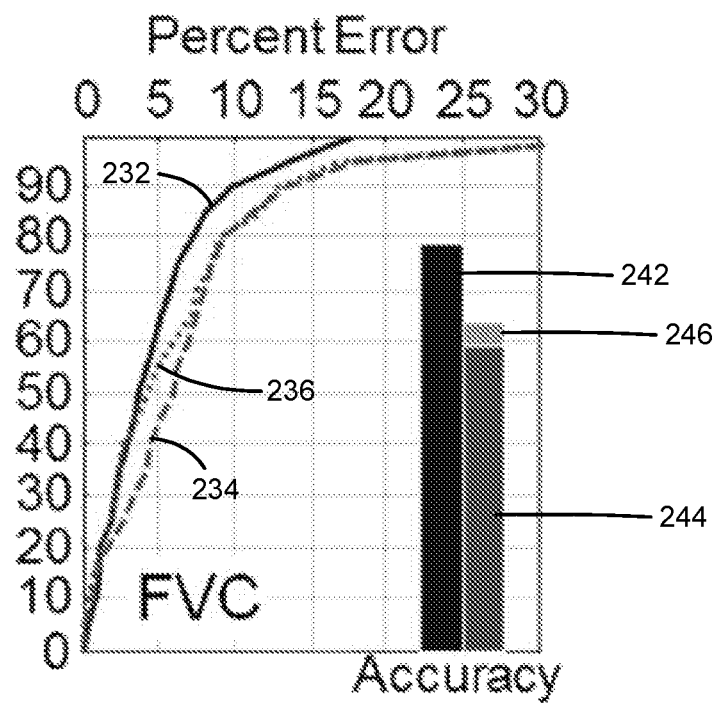
FIGS. 13A through 13D are cumulative percentage error plots for a smartphone-based spirometer, in accordance with many embodiments.
Figure 13B:
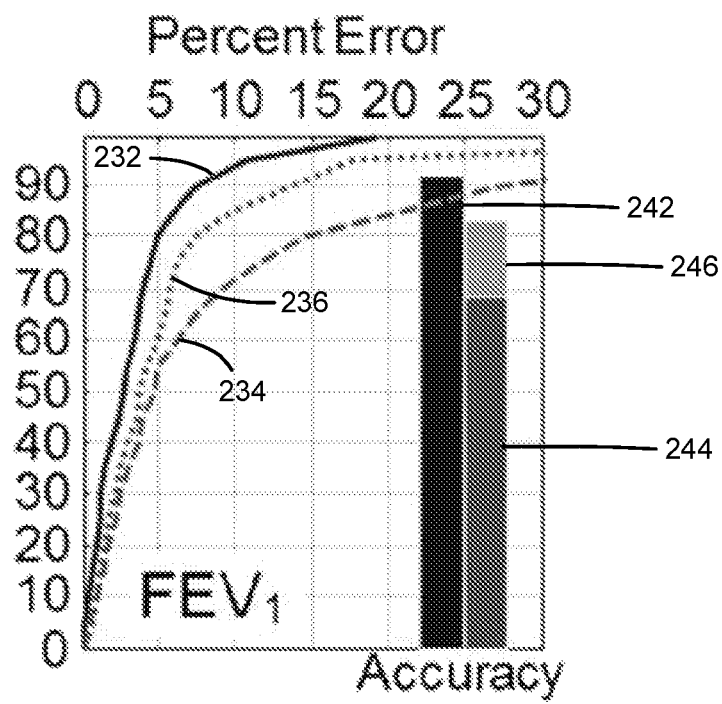
Figure 13C:
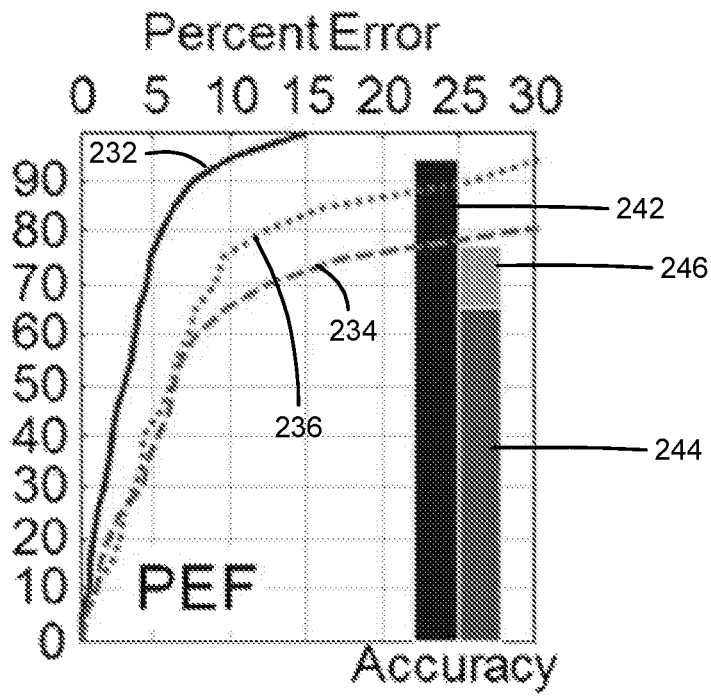
Figure 13D:
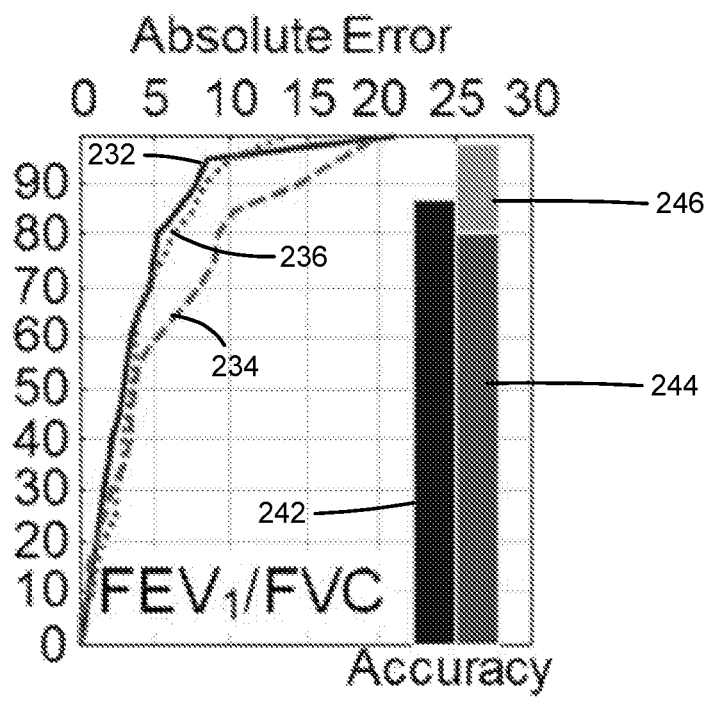

FIG. 12 is a simplified schematic diagram of a spirometric system 220 that includes a server 222 configured to remotely process a digital audio file of sounds of a subject's spirometric expiratory maneuver received from a remote device 224, so as to generate one or more spirometry curves and/or one or more related lung function parameters for the subject's spirometric expiratory maneuver. The server 220 includes a processor 226 and memory 228. In many embodiments, the memory 228 stores instructions executable by the processor 226 for causing the processor to process the digital audio file using any of the approaches as described herein so as to generate one or more spirometry curves and/or one or more related lung function parameters for the subject's spirometric expiratory maneuver. The resulting spirometry curves and/or related lung function parameters can then be utilized in any suitable fashion. For the resulting spirometry curves and/or related lung function parameters can then be at least one of (1) transmitted over the communication network (e.g., internet 230) to the remote device 224 for display and/or storage for future reference, (2) transmitted over the communication network to any other suitable device, for example, a remote device accessed by a treating professional, (3) stored in the memory 228 for future reference and/or use in processing other similar digital audio files, and (4) viewed via a website.

Empirical Results and Discussion

The performance of smartphone spirometer was compared to a clinical spirometer in terms of the accuracy of estimated lung function measures and false positive versus false negative readings. The ability to use the smartphone spirometer without a mouthpiece to control lip posture and/or a sling to control distance was assessed. The accuracy of the curves generated by the smartphone spirometer was assessed. And a comparison was made between diagnoses of pulmonologists based on spirometry tests performed using the smartphone spirometer and spirometry tests performed using a clinical spirometer. Based on the results of the foregoing assessments and comparisons, it was concluded that the smartphone spirometer will meet the needs of home lung function monitoring.

Estimate of Lung Function Measures

The comparison of measurements from the smartphone spirometer and the clinical spirometer were broken down by how the percent error is distributed and how well this conforms to accepted clinical variances in each measure.

Distribution of Percent Error in Lung Function Measures

FIG. 13A, FIG. 13B, FIG. 13C, and FIG. 13D present the cumulative percentage error plots for FVC, $FEV_1$, PEF, and $FEV_1$/FVC, respectively. The horizontal axis on the top shows the percent error between the actual and predicted value. The vertical axis shows the percentile of the lung function measures that are within that percent error. Hence, curves that approach the top left quickly are more accurate for a greater percentage of subjects. The results are categorized by normal subjects 232, abnormal subjects 234, and abnormal subjects whose models have been personalized 236.

For all lung function measures the spirometry approaches disclosed herein perform best on normal subjects, and abnormal distributions tend to have longer tails. The mean percent errors are 5.2%, 4.8%, 6.3%, and 4.0% for FVC, $FEV_1$, PEF, and $FEV_1$/FVC, respectively. When personalization is used, the mean percent errors improve to 5.0%, 3.5%, 4.6% and 3.6%. The personalized models significantly improve $FEV_1$, PEF, and $FEV_1$/FVC for abnormal subjects (based on an F-test of the residual variance, $p<0.05$), but do not significantly improve FVC. Personalized models for normal subjects (not shown) are not statistically significant.

The smartphone spirometer produces results that are consistent with other handheld spirometers, even without personalization (see, e.g., Rebuck, D. a., Hanania, N. a., D'Urzo, a. D., and Chapman, K. R. The Accuracy of a Handheld Portable Spirometer. *Chest* 109, 1 (1996); and Walters, J., Woodibaker, R., and Walls, J. Stability of the EasyOne ultrasonic spirometer for use in general practice. *Respirology* 11, 3 (2006)). While the accuracy of the smartphone spirometer is reduced for abnormal subjects as compared to normal subjects, it appears that personalization brings the error distributions for abnormal subjects much closer to that of normal subjects.

Accuracy of Lung Function Measures

Bar graphs 242, 244, 246 are also shown in FIG. 13A, FIG. 13B, FIG. 13C, and FIG. 13D to display the "accuracy" of each measure categorized by normal, abnormal, and abnormal-personalized, respectively. For FVC, $FEV_1$, and PEF, the accuracy was calculated by finding the number of measures that fall within a certain clinically relevant range. A range is used because the "actual value" of the measure is not specifically known. As previously discussed, a subject cannot simultaneously use a spirometer and the smartphone spirometer, so actual ground truth is unattainable. The range was calculated using ATS criteria for what constitutes a "reproducible" lung function measure. For example, a subject's FVC values can consistently be within 0.05 L or within 7% over short durations.

From the accuracies for the smartphone spirometer, it is apparent that, for normal individuals, FVC is within the range of expected variability almost 80% of the time and $FEV_1$ and PEF over 90% of the time. There is, however, a significant drop in accuracy for patients with abnormal lung function. Most subjects will almost always produce similar $FEV_1$ and PEF whether using the smartphone spirometer or a clinical spirometer. When abnormality is detected, personalization can be performed at a clinic to increase performance. FVC has the least accuracy and it appears personalization has little effect.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A handheld mobile device configured to generate expiratory flow-based pulmonary function data, the device comprising:
    a microphone operable to convert sound of a subject's forced expiratory maneuver into a digital data file, wherein the sound of the subject's forced expiratory maneuver includes sound projected from the subject's mouth without use of a mouthpiece during the subject's forced expiratory maneuver; and
    a processor operatively coupled with the microphone; and
    a data storage device operatively coupled with the processor and storing instructions that, when executed by the processor, cause the processor to process the digital data file to generate expiratory flow-based pulmonary function data for assessing pulmonary function of the subject including calculating at least one flow rate based on an estimated model of the subject's vocal tract and estimated reverberation of sound around the subject's head, wherein processing the digital data file includes at least one of the group consisting of: (1) compensating for estimated pressure losses sustained over a distance between the subject and the microphone, and (2) compensating for at least one of reverberations and reflections of sound of the forced expiratory maneuver.

2. The handheld mobile device of claim 1, wherein the sound of the subject's forced expiratory maneuver is converted into the digital data file without contact between the subject's mouth and the mobile device.

3. The handheld mobile device of claim 1, wherein the expiratory flow-based pulmonary function data includes at least one expiratory flow-based pulmonary function assessment parameter selected from the group consisting of: (1) Forced Vital Capacity (FVC), (2) Forced Expiratory Volume in one second (FEV1), (3) FEV1/FVC, (4) Peak Expiratory Flow (PEF), and (5) Forced Expiratory Flow between 25% and 75% of FVC (FEF(25-75)).

4. The handheld mobile device of claim 3, wherein the expiratory flow-based pulmonary function data includes at least one expiratory flow-based pulmonary function assessment metric that is based on at least one of the group consisting of: (1) FVC, (2) FEV1, (3) PEF, and (4) FEF(25-75).

5. The handheld mobile device of claim 1, wherein the expiratory flow-based pulmonary function data includes at least one expiratory flow-based pulmonary function assessment relationship selected from the group consisting of: (1) Flow vs. Time (FT), (2) Volume vs. Time (VT), and (3) Flow vs. Volume (FV).

6. The handheld mobile device of claim 1, wherein processing the digital data file includes modeling and removing superfluous sound generated by airflow of the forced expiratory maneuver.

7. The handheld mobile device of claim 6, wherein the superfluous sound is generated by airflow of the forced expiratory maneuver through at least one of the group consisting of: (1) the subject's vocal tract, (2) the subject's mouth, and (3) the subject's surrounding environment.

8. The handheld mobile device of claim 1, wherein processing the digital data file includes isolating at least one sound related to airflow of the forced expiratory maneuver and assessing intensity of the isolated at least one sound.

9. The handheld mobile device of claim 8, wherein the isolated at least one sound includes sound from at least one of the group consisting of: (1) wind shear, (2) vocal tract resonances, (3) wheezes, and (4) nasal resonances.

10. The handheld mobile device of claim 1, wherein processing the digital data file includes using inverse radiation modeling to at least one of the group consisting of: (1) compensate for estimated pressure losses sustained over a distance between the subject and the microphone, and (2) compensate for at least one of reverberations and reflections of sound of the forced expiratory maneuver.

11. The handheld mobile device of claim 1, wherein processing the digital data file includes removing the effects of AC-coupling by using at least one of the group consisting of: (1) signal power, (2) frequency characteristics, and (3) models of the subject's vocal tract.

12. The handheld mobile device of claim 1, wherein processing the digital data file includes removing non-linearity by combining at least two flow approximations based on the digital data file with one another.

13. The handheld mobile device of claim 1, wherein processing the digital data file includes using a global model that is based on a plurality of digital data files of sound recorded during different forced expiratory maneuvers.

14. The handheld mobile device of claim 13, wherein processing the digital data file includes generating Peak Expiratory Flow (PEF) and the global model comprises a global model of PEF rates of different expiratory maneuvers.

15. The handheld mobile device of claim 13, wherein processing the digital data file includes generating Forced Vital Capacity (FVC) and the global model comprises a global model of FVC values of different expiratory maneuvers.

16. The handheld mobile device of claim 13, wherein processing the digital data file includes generating Forced Expiratory Volume in one second (FEV1) and the global model comprises a global model of FEV1 values of different expiratory maneuvers.

17. The handheld mobile device of claim 1, wherein processing the digital data file includes calculating flow volume expelled through the subject's mouth by estimating flow velocity through the subject's mouth and flow area of the subject's mouth.

18. The handheld mobile device of claim 1, wherein processing the digital data file includes using a personalized model for a particular subject that is created by calibrating the expiratory flow-based pulmonary function data generated by the mobile device for the particular subject relative to expiratory flow-based pulmonary function data for the particular subject that is generated by another device.

19. The handheld mobile device of claim 1, wherein the digital data file is indicative of sound of the subject's unaided forced expiratory maneuver.

20. The handheld mobile device of claim 1, wherein the digital data file is indicative of sound pressure generated by the subject's forced expiratory maneuver.

* * * * *